(12) United States Patent
Udaykumar

(10) Patent No.: US 8,841,121 B2
(45) Date of Patent: Sep. 23, 2014

(54) VECTOR, VECTOR COMBINATIONS, METHODS AND KIT THEREOF

(75) Inventor: Ranga Udaykumar, Bangalore (IN)

(73) Assignee: Jawaharlal Nehru Centre for Advanced Scientific Research, Bangalore (IN)

( * ) Notice: Subject to any disclaimer, the term of this patent is extended or adjusted under 35 U.S.C. 154(b) by 0 days.

(21) Appl. No.: 13/809,758

(22) PCT Filed: Jul. 11, 2011

(86) PCT No.: PCT/IB2011/053081
§ 371 (c)(1),
(2), (4) Date: Jan. 11, 2013

(87) PCT Pub. No.: WO2012/007894
PCT Pub. Date: Jan. 19, 2012

(65) Prior Publication Data
US 2013/0109028 A1 May 2, 2013

(30) Foreign Application Priority Data

Jul. 12, 2010 (IN) .......................... 1973/CHE/2010

(51) Int. Cl.
*C12Q 1/68* (2006.01)
*C12Q 1/02* (2006.01)
*G01N 33/50* (2006.01)
*C12Q 1/18* (2006.01)

(52) U.S. Cl.
CPC .......... *C12Q 1/025* (2013.01); *G01N 2333/163* (2013.01); *G01N 33/5023* (2013.01); *C12Q 1/18* (2013.01)
USPC .................................................... 435/320.1

(58) Field of Classification Search
None
See application file for complete search history.

(56) References Cited

U.S. PATENT DOCUMENTS

2009/0217397 A1 8/2009 Stern et al.
2009/0247455 A1 10/2009 Fear

FOREIGN PATENT DOCUMENTS

WO   WO-2006102720 A1   10/2006
WO   WO-2007149246 A2   12/2007
WO   WO-2009139004 A2   11/2009

OTHER PUBLICATIONS

Niwa et al., Gene, 1991, vol. 108, pp. 193-199.*
*Aradopsis thaliana* T-DNA insertion sequence, 2008, downloaded from: http://www.ncbi.nlm.nih.gov/nuccore/197313391?sat=2&satkey=29780163.*
International Search Report and Written Opinion of the ISA, ISA/AU, mailed Apr. 10, 2011.

* cited by examiner

*Primary Examiner* — Michele K Joike
*Assistant Examiner* — Mindy G Brown
(74) *Attorney, Agent, or Firm* — Harness, Dickey & Pierce, PLC

(57) ABSTRACT

The disclosure relates to a method of identification of antiviral molecules that help in efficient viral control and thereby aid in disease management. In particular, the disclosure relates to identification of anti-Tat molecules and hence is directed towards antiviral drug development. The disclosure also relates to Tat-inducible GFP-anti RFP shRNA vector, vector combinations, recombinant cell having instant vectors, methods and kits thereof.

19 Claims, 19 Drawing Sheets
(16 of 19 Drawing Sheet(s) Filed in Color)

SEQUENCE LISTING

```
<160> NUMBER OF SEQ ID NOS: 20

<210> SEQ ID NO 1
<211> LENGTH: 6517
<212> TYPE: DNA
<213> ORGANISM: Artificial Sequence
<220> FEATURE:
<223> OTHER INFORMATION: pPRIME-LTR- 2GFP:anti-RFP miRNA (344) vector

<400> SEQUENCE: 1
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagtgca gacaaatggc agtattcatc cacaatttta aaagaaaagg     300
ggggattggg gggtacagtg cagggaaag aatagtagac ataatagcaa cagacataca     360
aactaaagaa ttacaaaaac aaattacaaa aattcaaaat tttcgggttt attacaggga     420
cagcagagat ccagtttggt tagtaccggg cccgctctag acgtattacc gccatgcatt     480
ggaagggcta atttggtccc aaaaaagaca agagatcctt gatctgtgga tctaccacac     540
acaaggctac ttccctgatt ggcagaacta cacaccaggg ccagggatca gatatccact     600
gacctttgga tggtgcttca agttagtacc agttgaacca gagcaagtag aagaggccaa     660
```

```
tgaaggagag  aacaacagct  tgttacaccc  tatgagccag  catgggatgg  aggacccgga   720
gggagaagta  ttagtgtgga  agtttgacag  cctcctagca  tttcgtcaca  tggcccgaga   780
gctgcatccg  gagtactaca  aagactgctg  acatcgagct  ttctacaagg  actttccgc    840 tggggacttt  ccagggaggt  gtggcctggg  cgggactggg  gagtggcgag  ccctcagatg   900
ctacatataa  gcagctgctt  tttgcctgta  ctgggtctct  ctggttagac  cagatctgag   960
cctgggagct  ctctggctaa  ctagggaacc  cactgcttaa  gcctcaataa  agcttgcctt  1020
gagtgctcaa  agtagtgtgt  gcccgtctgt  tgtgtgactc  tggtaactag  agatccctca  1080 gacccttta   gtcagtgtgg  aaaatctcta  gcaaccggtc  gccaccatgg  tgagcaaggg  1140
cgaggagctg  ttcaccgggg  tggtgcccat  cctggtcgag  ctggacggcg  acgtaaacgg  1200
ccacaagttc  agcgtgtccg  gcgagggcga  gggcgatgcc  acctacggca  agctgaccct  1260
gaagttcatc  tgcaccaccg  gcaagctgcc  cgtgccctgg  cccaccctcg  tgaccaccct  1320
gacctacggc  gtgcagtgct  tcagccgcta  ccccgaccac  atgaagcagc  acgacttctt  1380
caagtccgcc  atgcccgaag  gctacgtcca  ggagcgcacc  atcttcttca  aggacgacgg  1440
caactacaag  acccgcgccg  aggtgaagtt  cgagggcgac  accctggtga  accgcatcga  1500
gctgaagggc  atcgacttca  aggaggacgg  caacatcctg  gggcacaagc  tggagtacaa  1560
ctacaacagc  cacaacgtct  atatcatggc  cgacaagcag  aagaacggca  tcaaggtgaa  1620
cttcaagatc  cgccacaaca  tcgaggacgg  cagcgtgcag  ctcgccgacc  actaccagca  1680
gaacaccccc  atcggcgacg  gccccgtgct  gctgcccgac  aaccactacc  tgagcaccca  1740
gtccgccctg  agcaaagacc  ccaacgagaa  gcgcgatcac  atggtcctgc  tggagttcgt  1800
gaccgccgcc  gggatcactc  tcggcatgga  cgagctgtac  aagtagcggc  cgcaagcctt  1860
gttaagtgct  cgcttcggca  gcacatatac  tatgtttgaa  tgaggcttca  gtactttaca  1920
gaatcgttgc  ctgcacatct  tggaaacact  tgctgggatt  acttcttcag  gttaacccaa  1980
cagaaggctc  gagtgctgtt  gacagtgagc  gaacggctgc  ttcatctaca  aggttagtga  2040
agccacagat  gtaaccttgt  agatgaagca  gccgttgcct  actgcctcgg  agaattcaag  2100
gggctacttt  aggagcaatt  atcttgttta  ctaaaactga  ataccttgct  atctctttga  2160
tacattttta  caaagctgaa  ttaaaatggt  ataaattaaa  tcacttttt   caattggaag  2220 actaatgcgt  ttaaacacgc  ggcgacgcgt  tcgaccgaat  aaaacctgtg  acggaagatc  2280
acttcgcaga  ataaataaat  cctggtgtcc  ctgttgatac  cgggaagccc  tgggccaact  2340
tttggcgaaa  atgagacgtt  gatcggcacg  taagaggttc  caactttcac  cataatgaaa  2400
taagatcact  accgggcgta  ttttttgagt  tgtcgagatt  ttcaggagct  aaggaagcta  2460
aaatggagaa  aaaaatcact  ggatatacca  ccgttgatat  atcccaatgg  catcgtaaag  2520
aacattttga  ggcatttcag  tcagttgctc  aatgtaccta  taaccagacc  gttcagctgg  2580
atattacggc  cttttaaag   accgtaaaga  aaaataagca  caagtttat   ccggccttta  2640 ttcacattct  tgcccgcctg  atgaatgctc  atccggaatt  cgtatggca   atgaaagacg  2700 gtgagctggt  gatatgggat  agtgttcacc  cttgttacac  cgttttccat  gagcaaactg  2760
aaacgttttc  atcgctctgg  agtgaatacc  acgacgattt  ccggcagttt  ctacacatat  2820
attcgcaaga  tgtggcgtgt  tacggtgaaa  acctggccta  tttccctaaa  gggtttattg  2880
agaatatgtt  tttcgtctca  gccaatccct  gggtgagttt  caccagtttt  gatttaaacg  2940
tggccaatat  ggacaacttc  ttcgccccg   ttttcaccat  gggcaaatat  tatacgcaag  3000
gcgacaaggt  gctgatgccg  ctggcgattc  aggttcatca  tgccgtttgt  gatggcttcc  3060
```

```
atgtcggcag aatgcttaat gaattacaac agtactgcga tgagtggcag ggcggggcgt    3120
aattttttta aggcagttat tggtgccctt aaacgcctgg ttgctacgcc tgaataagtg    3180
ataataagcg gatgaatggc agaaattcgg atctcgaccg cgtttgggcg gtggctccct    3240
gccacgcggc tccgaacaga agctgatctc cgaagaggat ctgacatgtg tttaaacctc    3300
gacttaatta agtcgagggt cgacggtatc gataagctcg cttcacgaga tcatgtttaa    3360
gggttccggt tccactaggt acaattcgat atcaagctta tcgataatca acctctggat    3420
tacaaaattt gtgaaagatt gactggtatt cttaactatg ttgctccttt tacgctatgt    3480
ggatacgctg ctttaatgcc tttgtatcat gctattgctt cccgtatggc tttcattttc    3540
tcctccttgt ataaatcctg gttgctgtct ctttatgagg agttgtggcc cgttgtcagg    3600
caacgtggcg tggtgtgcac tgtgtttgct gacgcaaccc ccactggttg ggcattgcc    3660 accacctgtc agctcctttc cgggactttc gctttccccc tccctattgc cacggcggaa    3720
ctcatcgccg cctgccttgc ccgctgctgg acaggggctc ggctgttggg cactgacaat    3780
tccgtggtgt tgtcggggaa atcatcgtcc tttccttggc tgctcgcctg tgttgccacc    3840
tggattctgc gcgggacgtc cttctgctac gtcccttcgg ccctcaatcc agcggacctt    3900
ccttcccgcg gcctgctgcc ggctctgcgg cctcttccgc gtcttcgcct tcgccctcag    3960
acgagtcgga tctcccttg ggccgcctcc ccgcatcgat accgtcgacc tcgatcgaga    4020
cctagaaaaa catggagcaa tcacaagtag caatacagca gctaccaatg ctgattgtgc    4080
ctggctagaa gcacaagagg aggaggaggt gggttttcca gtcacacctc aggtaccttt    4140
aagaccaatg acttacaagg cagctgtaga tcttagccac ttttttaaaag aaaagggggg    4200 actggaaggg ctaattcact cccaacgaag acaagatatc cttgatctgt ggatctacca    4260
cacacaaggc tacttccctg attggcagaa ctacacacca gggccaggga tcagatatcc    4320
actgaccttt ggatggtgct acaagctagt accagttgag caagagaagg tagaagaagc    4380
caatgaagga gagaacaccc gcttgttaca ccctgtgagc ctgcatggga tggatgaccc    4440
ggagagagaa gtattagagt ggaggtttga cagccgccta gcatttcatc acatggcccg    4500
agagctgcat ccggactgta ctgggtctct ctggttagac cagatctgag cctgggagct    4560
ctctggctaa ctagggaacc cactgcttaa gcctcaataa agcttgcctt gagtgcttca    4620
agtagtgtgt gcccgtctgt tgtgtgactc tggtaactag agatccctca gcccttttta    4680
gtcagtgtgg aaaatctcta gcagcatgtg agcaaaaggc cagcaaaagg ccaggaaccg    4740
taaaaaggcc gcgttgctgg cgttttttcca taggctccgc cccctgacg agcatcacaa    4800 aaatcgacgc tcaagtcaga ggtggcgaaa cccgacagga ctataaagat accaggcgtt    4860 tcccctgga agctccctcg tgcgctctcc tgttccgacc ctgccgctta ccggatacct    4920
gtccgccttt ctcccttcgg gaagcgtggc gctttctcat agctcacgct gtaggtatct    4980
cagttcggtg taggtcgttc gctccaagct gggctgtgtg cacgaacccc ccgttcagcc    5040
cgaccgctgc gccttatccg gtaactatcg tcttgagtcc aacccggtaa gacacgactt    5100
atcgccactg gcagcagcca ctggtaacag gattagcaga gcgaggtatg taggcggtgc    5160
tacagagttc ttgaagtggt ggcctaacta cggctacact agaagaacag tatttggtat    5220
ctgcgctctg ctgaagccag ttaccttcgg aaaaagagtt ggtagctctt gatccggcaa    5280
acaaaccacc gctggtagcg gtggtttttt tgtttgcaag cagcagatta cgcgcagaaa    5340
aaaaggatct caagaagatc ctttgatctt ttctacgggg tctgacgctc agtggaacga    5400
```

| aaactcacgt taagggattt tggtcatgag attatcaaaa aggatcttca cctagatcct | 5460 |
| tttaaattaa aaatgaagtt ttaaatcaat ctaaagtata tatgagtaaa cttggtctga | 5520 |
| cagttaccaa tgcttaatca gtgaggcacc tatctcagcg atctgtctat ttcgttcatc | 5580 |
| catagttgcc tgactcccg tcgtgtagat aactacgata cgggagggct taccatctgg | 5640 |
| ccccagtgct gcaatgatac cgcgagaccc acgctcaccg gctccagatt tatcagcaat | 5700 |
| aaaccagcca gccggaaggg ccgagcgcag aagtggtcct gcaactttat ccgcctccat | 5760 |
| ccagtctatt aattgttgcc gggaagctag agtaagtagt tcgccagtta atagtttgcg | 5820 |
| caacgttgtt gccattgcta caggcatcgt ggtgtcacgc tcgtcgtttg gtatggcttc | 5880 |
| attcagctcc ggttcccaac gatcaaggcg agttacatga tcccccatgt tgtgcaaaaa | 5940 |
| agcggttagc tccttcggtc ctccgatcgt tgtcagaagt aagttggccg cagtgttatc | 6000 |
| actcatggtt atggcagcac tgcataattc tcttactgtc atgccatccg taagatgctt | 6060 |
| ttctgtgact ggtgagtact caaccaagtc attctgagaa tagtgtatgc ggcgaccgag | 6120 |
| ttgctcttgc ccggcgtcaa tacgggataa taccgcgcca catagcagaa ctttaaaagt | 6180 |
| gctcatcatt ggaaaacgtt cttcggggcg aaaactctca aggatcttac cgctgttgag | 6240 |
| atccagttcg atgtaaccca ctcgtgcacc caactgatct tcagcatctt ttactttcac | 6300 |
| cagcgtttct gggtgagcaa aaacaggaag gcaaaatgcc gcaaaaaagg gaataagggc | 6360 |
| gacacggaaa tgttgaatac tcatactctt cctttttcaa tattattgaa gcatttatca | 6420 |
| gggttattgt ctcatgagcg gatacatatt tgaatgtatt tagaaaaata aacaaatagg | 6480 |
| ggttccgcgc acatttcccc gaaaagtgcc acctgac | 6517 |

<210> SEQ ID NO 2
<211> LENGTH: 6517
<212> TYPE: DNA
<213> ORGANISM: Artificial Sequence
<220> FEATURE:
<223> OTHER INFORMATION: pPRIME-LTR-GFP: anti-RFP miRNA (miRNA 620) vector

<400> SEQUENCE: 2

| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt gcgctgcttc gcgatgtacg ggccagatat acgcgttgac | 240 |
| attgattatt gactagtgca gacaaatggc agtattcatc cacaatttta aaagaaaagg | 300 |
| ggggattggg gggtacagtg caggggaaag aatagtagac ataatagcaa cagacataca | 360 |
| aactaaagaa ttacaaaaac aaattacaaa aattcaaaat tttcgggttt attacaggga | 420 |
| cagcagagat ccagtttggt tagtaccggg cccgctctag acgtattacc gccatgcatt | 480 |
| ggaagggcta atttggtccc aaaaaagaca agagatcctt gatctgtgga tctaccacac | 540 |
| acaaggctac ttccctgatt ggcagaacta cacaccaggg ccagggatca gatatccact | 600 |
| gacctttgga tggtgcttca agttagtacc agttgaacca gagcaagtag aagaggccaa | 660 |
| tgaaggagag aacaacagct tgttacaccc tatgagccag catgggatgg aggacccgga | 720 |
| gggagaagta ttagtgtgga gtttgacag cctcctagca tttcgtcaca tggcccgaga | 780 |
| gctgcatccg gagtactaca agactgctg acatcgagct ttctacaagg acttttccgc | 840 |
| tggggacttt ccaggggagt gtggcctggg cgggactggg gagtggcgag ccctcagatg | 900 |

```
ctacatataa gcagctgctt tttgcctgta ctgggtctct ctggttagac cagatctgag      960
cctgggagct ctctggctaa ctagggaacc cactgcttaa gcctcaataa agcttgcctt     1020
gagtgctcaa agtagtgtgt gcccgtctgt tgtgtgactc tggtaactag agatccctca     1080
gacccttta gtcagtgtgg aaaatctcta gcaaccggtc gccaccatgg tgagcaaggg     1140
cgaggagctg ttcaccgggg tggtgcccat cctggtcgag ctggacggcg acgtaaacgg     1200
ccacaagttc agcgtgtccg gcgagggcga gggcgatgcc acctacggca agctgaccct     1260
gaagttcatc tgcaccaccg gcaagctgcc cgtgccctgg cccaccctcg tgaccaccct     1320
gacctacggc gtgcagtgct tcagccgcta ccccgaccac atgaagcagc acgacttctt     1380
caagtccgcc atgcccgaag gctacgtcca ggagcgcacc atcttcttca aggacgacgg     1440
caactacaag acccgcgccg aggtgaagtt cgagggcgac accctggtga accgcatcga     1500
gctgaagggc atcgacttca aggaggacgg caacatcctg ggcacaagc tggagtacaa     1560
ctacaacagc cacaacgtct atatcatggc cgacaagcag aagaacggca tcaaggtgaa     1620
cttcaagatc cgccacaaca tcgaggacgg cagcgtgcag ctcgccgacc actaccagca     1680
gaacaccccc atcggcgacg gccccgtgct gctgcccgac aaccactacc tgagcaccca     1740
gtccgccctg agcaaagacc ccaacgagaa gcgcgatcac atggtcctgc tggagttcgt     1800
gaccgccgcc gggatcactc tcggcatgga cgagctgtac aagtagcggc cgcaagcctt     1860
gttaagtgct cgcttcggca gcacatatac tatgtttgaa tgaggcttca gtactttaca     1920
gaatcgttgc ctgcacatct tggaaacact tgctgggatt acttcttcag gttaacccaa     1980
cagaaggctc gagtgctgtt gacagtgagc gaactacacc atcgtggagc agtatagtga     2040
agccacagat gtatactgct ccacgatggt gtagttgcct actgcctcgg agaattcaag     2100
gggctacttt aggagcaatt atcttgttta ctaaaactga ataccttgct atctctttga     2160
tacatttta caaagctgaa ttaaaatggt ataaattaaa tcactttttt caattggaag     2220
actaatgcgt ttaaacacgc ggcgacgcgt tcgaccgaat aaaacctgtg acggaagatc     2280
acttcgcaga ataaataaat cctggtgtcc ctgttgatac cgggaagccc tgggccaact     2340
tttggcgaaa atgagacgtt gatcggcacg taagaggttc caactttcac cataatgaaa     2400
taagatcact accgggcgta ttttttgagt tgtcgagatt ttcaggagct aaggaagcta     2460
aaatggagaa aaaaatcact ggatatacca ccgttgatat atcccaatgg catcgtaaag     2520
aacattttga ggcatttcag tcagttgctc aatgtaccta taaccagacc gttcagctgg     2580
atattacggc ctttttaaag accgtaaaga aaaataagca caagttttat ccggccttta     2640
ttcacattct tgcccgcctg atgaatgctc atccggaatt acgtatggca atgaaagacg     2700
gtgagctggt gatatgggat agtgttcacc cttgttacac cgttttccat gagcaaactg     2760
aaacgttttc atcgctctgg agtgaatacc acgacgattt ccggcagttt ctacacatat     2820
attcgcaaga tgtggcgtgt tacggtgaaa acctggccta tttccctaaa gggtttattg     2880
agaatatgtt tttcgtctca gccaatccct gggtgagttt caccagtttt gatttaaacg     2940
tggccaatat ggacaacttc ttcgccccg ttttcaccat gggcaaatat tatacgcaag     3000
gcgacaaggt gctgatgccg ctggcgattc aggttcatca tgccgtttgt gatggcttcc     3060
atgtcggcag aatgcttaat gaattacaac agtactgcga tgagtggcag gcggggcgt     3120
aattttttta aggcagttat tggtgccctt aaacgcctgg ttgctacgcc tgaataagtg     3180
ataataagcg gatgaatggc agaaattcgg atctcgaccg cgtttgggcg gtggctcct     3240
gccacgcggc tccgaacaga agctgatctc cgaagaggat ctgacatgtg tttaaacctc     3300
```

```
gacttaatta agtcgagggt cgacggtatc gataagctcg cttcacgaga tcatgtttaa    3360
gggttccggt tccactaggt acaattcgat atcaagctta tcgataatca acctctggat    3420
tacaaaattt gtgaaagatt gactggtatt cttaactatg ttgctccttt tacgctatgt    3480
ggatacgctg ctttaatgcc tttgtatcat gctattgctt cccgtatggc tttcattttc    3540
tcctccttgt ataaatcctg gttgctgtct ctttatgagg agttgtggcc cgttgtcagg    3600
caacgtggcg tggtgtgcac tgtgtttgct gacgcaaccc ccactggttg gggcattgcc    3660
accacctgtc agctcctttc cgggactttc gctttccccc tcctattgc cacggcggaa     3720 ctcatcgccg cctgccttgc ccgctgctgg acaggggctc ggctgttggg cactgacaat    3780
tccgtggtgt tgtcggggaa atcatcgtcc tttccttggc tgctcgcctg tgttgccacc    3840
tggattctgc gcgggacgtc cttctgctac gtcccttcgg ccctcaatcc agcggacctt    3900
ccttcccgcg gcctgctgcc ggctctgcgg cctcttccgc gtcttcgcct tcgccctcag    3960
acgagtcgga tctcccttg ggccgcctcc ccgcatcgat accgtcgacc tcgatcgaga     4020
cctagaaaaa catggagcaa tcacaagtag caatacagca gctaccaatg ctgattgtgc    4080
ctggctagaa gcacaagagg aggaggaggt gggttttcca gtcacacctc aggtaccttt    4140
aagaccaatg acttacaagg cagctgtaga tcttagccac ttttttaaaag aaaagggggg    4200 actggaaggg ctaattcact cccaacgaag acaagatatc cttgatctgt ggatctacca    4260
cacacaaggc tacttccctg attggcagaa ctacacacca gggccaggga tcagatatcc    4320
actgaccttt ggatggtgct acaagctagt accagttgag caagagaagg tagaagaagc    4380
caatgaagga gagaacaccc gcttgttaca ccctgtgagc ctgcatggga tggatgaccc    4440
ggagagagaa gtattagagt ggaggtttga cagccgccta gcatttcatc acatggcccg    4500
agagctgcat ccggactgta ctgggtctct ctggttagac cagatctgag cctgggagct    4560
ctctggctaa ctagggaacc cactgcttaa gcctcaataa agcttgcctt gagtgcttca    4620
agtagtgtgt gcccgtctgt tgtgtgactc tggtaactag agatccctca gacccttta     4680 gtcagtgtgg aaaatctcta gcagcatgtg agcaaaaggc cagcaaaagg ccaggaaccg    4740
taaaaaggcc gcgttgctgg cgttttttcca taggctccgc cccctgacg agcatcacaa     4800 aaatcgacgc tcaagtcaga ggtggcgaaa cccgacagga ctataaagat accaggcgtt    4860
tccccctgga agctccctcg tgcgctctcc tgttccgacc ctgccgctta ccggatacct    4920
gtccgccttt ctcccttcgg gaagcgtggc gctttctcat agctcacgct gtaggtatct    4980
cagttccggt taggtcgttc gctccaagct gggctgtgtg cacgaacccc ccgttcagcc    5040
cgaccgctgc gccttatccg gtaactatcg tcttgagtcc aacccggtaa gacacgactt    5100
atcgccactg gcagcagcca ctggtaacag gattagcaga gcgaggtatg taggcggtgc    5160
tacagagttc ttgaagtggt ggcctaacta cggctacact agaagaacag tatttggtat    5220
ctgcgctctg ctgaagccag ttaccttcgg aaaaagagtt ggtagctctt gatccggcaa    5280
acaaaccacc gctggtagcg tggtttttt tgtttgcaag cagcagatta cgcgcagaaa     5340
aaaaggatct caagaagatc ctttgatctt ttctacgggg tctgacgctc agtggaacga    5400
aaactcacgt taagggattt tggtcatgag attatcaaaa aggatcttca cctagatcct    5460
tttaaattaa aaatgaagtt ttaaatcaat ctaaagtata tatgagtaaa cttggtctga    5520
cagttaccaa tgcttaatca gtgaggcacc tatctcagcg atctgtctat ttcgttcatc    5580
catagttgcc tgactccccg tcgtgtagat aactacgata cgggagggct taccatctgg    5640
```

```
ccccagtgct gcaatgatac cgcgagaccc acgctcaccg gctccagatt tatcagcaat    5700
aaaccagcca gccggaaggg ccgagcgcag aagtggtcct gcaactttat ccgcctccat    5760
ccagtctatt aattgttgcc gggaagctag agtaagtagt tcgccagtta atagtttgcg    5820
caacgttgtt gccattgcta caggcatcgt ggtgtcacgc tcgtcgtttg gtatggcttc    5880
attcagctcc ggttcccaac gatcaaggcg agttacatga tcccccatgt tgtgcaaaaa    5940
agcggttagc tccttcggtc ctccgatcgt tgtcagaagt aagttggccg cagtgttatc    6000
actcatggtt atggcagcac tgcataattc tcttactgtc atgccatccg taagatgctt    6060
ttctgtgact ggtgagtact caaccaagtc attctgagaa tagtgtatgc ggcgaccgag    6120
ttgctcttgc ccggcgtcaa tacgggataa taccgcgcca catagcagaa ctttaaaagt    6180
gctcatcatt ggaaaacgtt cttcggggcg aaaactctca aggatcttac cgctgttgag    6240
atccagttcg atgtaaccca ctcgtgcacc caactgatct tcagcatctt ttactttcac    6300
cagcgtttct gggtgagcaa aaacaggaag gcaaaatgcc gcaaaaaagg gaataagggc    6360
gacacggaaa tgttgaatac tcatactctt cctttttcaa tattattgaa gcatttatca    6420
gggttattgt ctcatgagcg gatacatatt tgaatgtatt tagaaaaata aacaaatagg    6480
ggttccgcgc acatttcccc gaaaagtgcc acctgac                             6517

<210> SEQ ID NO 3
<211> LENGTH: 8566
<212> TYPE: DNA
<213> ORGANISM: Artificial Sequence
<220> FEATURE:
<223> OTHER INFORMATION: pPRIME-CMV-GFP-FF3 - Original Base vector

<400> SEQUENCE: 3
gcgtggatag cggtttgact cacggggatt tccaagtctc cacccccattg acgtcaatgg      60 gagtttgttt tggcaccaaa atcaacggga ctttccaaaa tgtcgtaaca actccgcccc     120
attgacgcaa atgggcggta ggcgtgtacg gtgggaggtc tatataagca gagctggttt     180
agtgaaccgt cagatccgct agcgctaccg gtcgccacca tggtgagcaa gggcgaggag     240
ctgttcaccg gggtggtgcc catcctggtc gagctggacg gcgacgtaaa cggccacaag     300
ttcagcgtgt ccggcgaggg cgagggcgat gccacctacg gcaagctgac cctgaagttc     360
atctgcacca ccggcaagct gcccgtgccc tggcccaccc tcgtgaccac cctgacctac     420
ggcgtgcagt gcttcagccg ctaccccgac cacatgaagc agcacgactt cttcaagtcc     480
gccatgcccg aaggctacgt ccaggagcgc accatcttct tcaaggacga cggcaactac     540
aagacccgcg ccgaggtgaa gttcgagggc gacaccctgg tgaaccgcat cgagctgaag     600
ggcatcgact tcaaggagga cggcaacatc ctggggcaca agctggagta caactacaac     660
agccacaacg tctatatcat ggccgacaag cagaagaacg gcatcaaggt gaacttcaag     720
atccgccaca acatcgagga cggcagcgtg cagctcgccg accactacca gcagaacacc     780
cccatcggcg acggccccgt gctgctgccc gacaaccact acctgagcac ccagtccgcc     840
ctgagcaaag accccaacga gaagcgcgat cacatggtcc tgctggagtt cgtgaccgcc     900
gccgggatca ctctcggcat ggacgagctg tacaagtagc ggccgcaagc cttgttaagt     960
gctcgcttcg gcagcacata tactatgttt gaatgaggct tcagtacttt acagaatcgt    1020
tgcctgcaca tcttggaaac acttgctggg attacttctt caggttaacc aacagaagg     1080 ctcgagagct cccgctgaat tggaatccta gtgaagccac agatgtagga ttccaattca    1140
gcgggagccg aattcaaggg gctactttag gagcaattat cttgtttact aaaactgaat    1200
```

```
accttgctat ctctttgata catttttaca aagctgaatt aaaatggtat aaattaaatc    1260
acttttttca attggaagac taatgcgttt aaacacgcgg cgacgcgttc gaccgaataa    1320
aacctgtgac ggaagatcac ttcgcagaat aaataaatcc tggtgtccct gttgataccg    1380
ggaagccctg ggccaacttt tggcgaaaat gagacgttga tcggcacgta agaggttcca    1440
actttcacca taatgaaata agatcactac cgggcgtatt ttttgagttg tcgagatttt    1500
caggagctaa ggaagctaaa atggagaaaa aatcactgg atataccacc gttgatatat     1560
cccaatggca tcgtaaagaa cattttgagg catttcagtc agttgctcaa tgtacctata    1620
accagaccgt tcagctggat attacggcct ttttaaagac cgtaaagaaa aataagcaca    1680
agttttatcc ggcctttatt cacattcttg cccgcctgat gaatgctcat ccggaattac    1740
gtatggcaat gaaagacggt gagctggtga tatgggatag tgttcaccct tgttacaccg    1800
ttttccatga gcaaactgaa acgttttcat cgctctggag tgaataccac gacgatttcc    1860
ggcagtttct acacatatat tcgcaagatg tggcgtgtta cggtgaaaac ctggcctatt    1920
tccctaaagg gtttattgag aatatgtttt tcgtctcagc caatccctgg gtgagtttca    1980
ccagttttga tttaaacgtg gccaatatgg acaacttctt cgccccgtt ttcaccatgg      2040 gcaaatatta tacgcaaggc gacaaggtgc tgatgccgct ggcgattcag gttcatcatg    2100
ccgtttgtga tggcttccat gtcggcagaa tgcttaatga attacaacag tactgcgatg    2160
agtggcaggg cggggcgtaa tttttttaag gcagttattg gtgcccttaa acgcctggtt    2220
gctacgcctg aataagtgat aataagcgga tgaatggcag aaattcggat ctcgaccgcg    2280
tttgggcggt ggctccctgc cacgcggctc cgaacagaag ctgatctccg aagaggatct    2340
gacatgtgtt taaacctcga cttaattaag tcgagggtcg acggtatcga taagctcgct    2400
tcacgagatc atgtttaagg gttccggttc cactaggtac aattcgatat caagcttatc    2460
gataatcaac ctctggatta caaaatttgt gaaagattga ctggtattct taactatgtt    2520
gctcctttta cgctatgtgg atacgctgct ttaatgcctt tgtatcatgc tattgcttcc    2580
cgtatggctt tcatttctc ctccttgtat aaatcctggt tgctgtctct ttatgaggag     2640
ttgtggcccg ttgtcaggca acgtggcgtg gtgtgcactg tgtttgctga cgcaacccc    2700 actggttggg gcattgccac cacctgtcag ctcctttccg ggactttcgc tttccccctc    2760
cctattgcca cggcggaact catcgccgcc tgccttgccc gctgctggac aggggctcgg    2820
ctgttgggca ctgacaattc cgtggtgttg tcggggaaat catcgtcctt ccttggctg    2880 ctcgcctgtg ttgccacctg gattctgcgc gggacgtcct tctgctacgt cccttcggcc    2940
ctcaatccag cggaccttcc ttcccgcggc ctgctgccgg ctctgcggcc tcttccgcgt    3000
cttcgccttc gccctcagac gagtcggatc tccctttggg ccgcctcccc gcatcgatac    3060
cgtcgacctc gatcgagacc tagaaaaaca tggagcaatc acaagtagca atacagcagc    3120
taccaatgct gattgtgcct ggctagaagc acaagaggag gaggaggtgg gttttccagt    3180
cacacctcag gtacctttaa gaccaatgac ttacaaggca gctgtagatc ttagccactt    3240
tttaaaagaa aagggggac tggaagggct aattcactcc caacgaagac aagatatcct     3300
tgatctgtgg atctaccaca cacaaggcta cttccctgat tggcagaact acacaccagg    3360
gccagggatc agatatccac tgacctttgg atggtgctac aagctagtac cagttgagca    3420
agagaaggta gaagaagcca atgaaggaga gaacacccgc ttgttacacc ctgtgagcct    3480
gcatgggatg gatgacccgg agagagaagt attagagtgg aggtttgaca gccgcctagc    3540
```

-continued

| | | | | | |
|---|---|---|---|---|---|
| atttcatcac | atggcccgag | agctgcatcc | ggactgtact | gggtctctct | ggttagacca | 3600 |
| gatctgagcc | tgggagctct | ctggctaact | agggaaccca | ctgcttaagc | ctcaataaag | 3660 |
| cttgccttga | gtgcttcaag | tagtgtgtgc | ccgtctgttg | tgtgactctg | gtaactagag | 3720 |
| atccctcaga | cccttttagt | cagtgtggaa | aatctctagc | agcatgtgag | caaaaggcca | 3780 |
| gcaaaaggcc | aggaaccgta | aaaaggccgc | gttgctggcg | ttttttccata | ggctccgccc | 3840 |
| ccctgacgag | catcacaaaa | atcgacgctc | aagtcagagg | tggcgaaacc | cgacaggact | 3900 |
| ataaagatac | caggcgtttc | cccctggaag | ctccctcgtg | cgctctcctg | ttccgaccct | 3960 |
| gccgcttacc | ggatacctgt | ccgcctttct | cccttcggga | agcgtggcgc | tttctcatag | 4020 |
| ctcacgctgt | aggtatctca | gttcggtgta | ggtcgttcgc | tccaagctgg | gctgtgtgca | 4080 |
| cgaaccccc | gttcagcccg | accgctgcgc | cttatccggt | aactatcgtc | ttgagtccaa | 4140 |
| cccggtaaga | cacgacttat | cgccactggc | agcagccact | ggtaacagga | ttagcagagc | 4200 |
| gaggtatgta | ggcggtgcta | cagagttctt | gaagtggtgg | cctaactacg | gctacactag | 4260 |
| aagaacagta | tttggtatct | gcgctctgct | gaagccagtt | accttcggaa | aaagagttgg | 4320 |
| tagctcttga | tccggcaaac | aaaccaccgc | tggtagcggt | ggttttttg | tttgcaagca | 4380 |
| gcagattacg | cgcagaaaaa | aaggatctca | agaagatcct | ttgatctttt | ctacggggtc | 4440 |
| tgacgctcag | tggaacgaaa | actcacgtta | agggattttg | gtcatgagat | tatcaaaaag | 4500 |
| gatcttcacc | tagatccttt | taaattaaaa | atgaagtttt | aaatcaatct | aaagtatata | 4560 |
| tgagtaaact | tggtctgaca | gttaccaatg | cttaatcagt | gaggcaccta | tctcagcgat | 4620 |
| ctgtctattt | cgttcatcca | tagttgcctg | actccccgtc | gtgtagataa | ctacgatacg | 4680 |
| ggagggctta | ccatctggcc | ccagtgctgc | aatgataccg | cgagacccac | gctcaccggc | 4740 |
| tccagattta | tcagcaataa | accagccagc | cggaagggcc | gagcgcagaa | gtggtcctgc | 4800 |
| aactttatcc | gcctccatcc | agtctattaa | ttgttgccgg | gaagctagag | taagtagttc | 4860 |
| gccagttaat | agtttgcgca | acgttgttgc | cattgctaca | ggcatcgtgg | tgtcacgctc | 4920 |
| gtcgtttggt | atggcttcat | tcagctccgg | ttcccaacga | tcaaggcgag | ttacatgatc | 4980 |
| ccccatgttg | tgcaaaaaag | cggttagctc | cttcggtcct | ccgatcgttg | tcagaagtaa | 5040 |
| gttggccgca | gtgttatcac | tcatggttat | ggcagcactg | cataattctc | ttactgtcat | 5100 |
| gccatccgta | agatgctttt | ctgtgactgg | tgagtactca | accaagtcat | tctgagaata | 5160 |
| gtgtatgcgg | cgaccgagtt | gctcttgccc | ggcgtcaata | cgggataata | ccgcgccaca | 5220 |
| tagcagaact | ttaaaagtgc | tcatcattgg | aaaacgttct | tcggggcgaa | aactctcaag | 5280 |
| gatcttaccg | ctgttgagat | ccagttcgat | gtaacccact | cgtgcaccca | actgatcttc | 5340 |
| agcatctttt | actttcacca | gcgtttctgg | gtgagcaaaa | acaggaaggc | aaaatgccgc | 5400 |
| aaaaaggga | ataagggcga | cacggaaatg | ttgaatactc | atactcttcc | tttttcaata | 5460 |
| ttattgaagc | atttatcagg | gttattgtct | catgagcgga | tacatatttg | aatgtattta | 5520 |
| gaaaaataaa | caaataggg | ttccgcgcac | atttccccga | aaagtgccac | ctgacgtcga | 5580 |
| cggatcggga | gatctcccga | tcccctatgg | tgcactctca | gtacaatctg | ctctgatgcc | 5640 |
| gcatagttaa | gccagtatct | gctccctgct | tgtgtgttgg | aggtcgctga | gtagtgcgcg | 5700 |
| agcaaaattt | aagctacaac | aaggcaaggc | ttgaccgaca | attgcatgaa | gaatctgctt | 5760 |
| agggttaggc | gttttgcgct | gcttcgcgat | gtacgggcca | gatatacgcg | ttgacattga | 5820 |
| ttattgacta | gttattaata | gtaatcaatt | acggggtcat | tagttcatag | cccatatatg | 5880 |
| gagttccgcg | ttacataact | tacggtaaat | ggcccgcctg | gctgaccgcc | caacgacccc | 5940 |

```
cgcccattga cgtcaataat gacgtatgtt cccatagtaa cgccaatagg gactttccat    6000
tgacgtcaat gggtggagta tttacggtaa actgcccact tggcagtaca tcaagtgtat    6060
catatgccaa gtacgccccc tattgacgtc aatgacggta aatggcccgc ctggcattat    6120
gcccagtaca tgaccttatg ggactttcct acttggcagt acatctacgt attagtcatc    6180
gctattacca tggtgatgcg gttttggcag tacatcaatg ggcgtggata gcggtttgac    6240
tcacggggat ttccaagtct ccaccccatt gacgtcaatg ggagtttgtt ttggcaccaa    6300
aatcaacggg actttccaaa atgtcgtaac aactccgccc cattgacgca aatgggcggt    6360
aggcgtgtac ggtgggaggt ctatagacca gatctgagcc tgggagctct ctggctaact    6420
agggaaccca ctgcttaagc ctcaataaag cttgccttga gtgcttcaag tagtgtgtgc    6480
ccgtctgttg tgtgactctg gtaactagag atccctcaga ccctttttagt cagtgtggaa    6540 aatctctagc agtggcgccc gaacagggac ttgaaagcga agggaaaacc agaggagctc    6600
tctcgacgca ggactcggct tgctgaagcg cgcacggcaa gaggcgaggg gcggcgactg    6660
gtgagtacgc caaaaatttt gactagcgga ggctagaagg agagagatgg gtgcgagagc    6720
gtcagtatta agcgggggag aattagatcg cgatgggaaa aaattcggtt aaggccaggg    6780
ggaaagaaaa aatataaata aacatatagt atgggcaagc agggagctag aacgattcgc    6840
agttaatcct ggcctgttag aaacatcaga aggctgtaga caaatactgg gacagctaca    6900
accatccctt cagacaggat cagaagaact tagatcatta taatacag tagcaaccct    6960 ctattgtgtg catcaaagga tagagataaa agacaccaag gaagctttag acaagataga    7020
ggaagagcaa aacaaaagta agaccaccgc acagcaagcg gccggccgcg ctgatcttca    7080
gacctggagg aggagatatg agggacaatt ggagaagtga attatataaa tataaagtag    7140
taaaaattga accattagga gtagcaccca ccaaggcaaa gagaagagtg gtgcagagag    7200
aaaaaagagc agtgggaata ggagctttgt tccttgggtt cttggagca gcaggaagca    7260 ctatgggcgc agcgtcaatg acgctgacgg tacaggccag acaattattg tctggtatag    7320
tgcagcagca gaacaatttg ctgagggcta ttgaggcgca acagcatctg ttgcaactca    7380
cagtctgggg catcaagcag ctccaggcaa gaatcctggc tgtggaaaga tacctaaagg    7440
atcaacagct cctggggatt tggggttgct ctggaaaact catttgcacc actgctgtgc    7500
cttggaatgc tagttggagt aataaatctc tggaacagat ttggaatcac acgacctgga    7560
tggagtggga cagagaaatt aacaattaca caagcttaat acactcctta attgaagaat    7620
cgcaaaacca gcaagaaaag aatgaacaag aattattgga attagataaa tgggcaagtt    7680
tgtggaattg gtttaacata acaaattggc tgtggtatat aaaattattc ataatgatag    7740
taggaggctt ggtaggttta agaatagttt ttgctgtact ttctatagtg aatagagtta    7800
ggcagggata ttcaccatta tcgtttcaga cccacctccc aaccccgagg ggacccgaca    7860
ggcccgaagg aatagaagaa gaaggtggag agagagacag agacagatcc attcgattag    7920
tgaacggatc ggcactgcgt gcgccaattc tgcagacaaa tggcagtatt catccacaat    7980
tttaaaagaa aagggggggat tggggggtac agtgcagggg aaagaatagt agacataata    8040
gcaacagaca tacaaactaa agaattacaa aaacaaatta caaaaattca aaattttcgg    8100
gtttattaca gggacagcag agatccagtt tggttagtac cgggcccgct ctagacgtat    8160
taccgccatg cattagttat taatagtaat caattacggg gtcattagtt catagcccat    8220
atatggagtt ccgcgttaca taacttacgg taaatggccc gcctggctga ccgcccaacg    8280
```

```
acccccgccc attgacgtca ataatgacgt atgttcccat agtaacgcca atagggactt    8340
tccattgacg tcaatgggtg gagtatttac ggtaaactgc ccacttggca gtacatcaag    8400
tgtatcatat gccaagtacg ccccctattg acgtcaatga cggtaaatgg cccgcctggc    8460
attatgccca gtacatgacc ttatgggact ttcctacttg gcagtacatc tacgtattag    8520
tcatcgctat taccatggtg atgcggtttt ggcagtacat caatgg                  8566
```

```
<210> SEQ ID NO 4
<211> LENGTH: 22
<212> TYPE: DNA
<213> ORGANISM: Artificial Sequence
<220> FEATURE:
<223> OTHER INFORMATION: shRNA (miRNA 344)

<400> SEQUENCE: 4
acggctgctt catctacaag gt                                              22

<210> SEQ ID NO 5
<211> LENGTH: 22
<212> TYPE: DNA
<213> ORGANISM: Artificial Sequence
<220> FEATURE:
<223> OTHER INFORMATION: shRNA (miRNA 620)

<400> SEQUENCE: 5
actacaccat cgtggagcag ta                                              22

<210> SEQ ID NO 6
<211> LENGTH: 22
<212> TYPE: DNA
<213> ORGANISM: Artificial Sequence
<220> FEATURE:
<223> OTHER INFORMATION: shRNA (miRNA p603)

<400> SEQUENCE: 6
ccctgccctt cccctgggac at                                              22

<210> SEQ ID NO 7
<211> LENGTH: 22
<212> TYPE: DNA
<213> ORGANISM: Artificial Sequence
<220> FEATURE:
<223> OTHER INFORMATION: shRNA (miRNA 14)

<400> SEQUENCE: 7
agaacgtcat caccgagttc at                                              22

<210> SEQ ID NO 8
<211> LENGTH: 22
<212> TYPE: DNA
<213> ORGANISM: Artificial Sequence
<220> FEATURE:
<223> OTHER INFORMATION: shRNA (miRNA 515)

<400> SEQUENCE: 8
actacctggt ggagttcaag tc                                              22

<210> SEQ ID NO 9
<211> LENGTH: 33
<212> TYPE: DNA
<213> ORGANISM: Artificial Sequence
<220> FEATURE:
<223> OTHER INFORMATION: N668 Forward Primer

<400> SEQUENCE: 9
```
ctagtaggta ccatggcctc ctccgagaac gtc                                    33

<210> SEQ ID NO 10
<211> LENGTH: 33
<212> TYPE: DNA
<213> ORGANISM: Artificial Sequence
<220> FEATURE:
<223> OTHER INFORMATION: N669 Reverse Primer

<400> SEQUENCE: 10
agccgttcta gactacagga acaggtggtg gcg                                    33

<210> SEQ ID NO 11
<211> LENGTH: 41
<212> TYPE: DNA
<213> ORGANISM: Artificial Sequence
<220> FEATURE:
<223> OTHER INFORMATION: N113 Forward Primer

<400> SEQUENCE: 11
tagaattcgc cgccgccatg gagccagtag atcctaacct a                           41

<210> SEQ ID NO 12
<211> LENGTH: 36
<212> TYPE: DNA
<213> ORGANISM: Artificial Sequence
<220> FEATURE:
<223> OTHER INFORMATION: N531 Reverse Primer

<400> SEQUENCE: 12
agaagcggat ccctaatgga ccggatctgt ctctgt                                 36

<210> SEQ ID NO 13
<211> LENGTH: 21
<212> TYPE: RNA
<213> ORGANISM: Artificial Sequence
<220> FEATURE:
<223> OTHER INFORMATION: siRNA: N1398-9 (1)
<220> FEATURE:
<221> NAME/KEY: dTdT
<222> LOCATION: (20)..(21)

<400> SEQUENCE: 13
cugcuuguac caauugcuat t                                                 21

<210> SEQ ID NO 14
<211> LENGTH: 21
<212> TYPE: RNA
<213> ORGANISM: Artificial Sequence
<220> FEATURE:
<223> OTHER INFORMATION: siRNA: N1398-9 (2)
<220> FEATURE:
<221> NAME/KEY: dTdT
<222> LOCATION: (20)..(21)

<400> SEQUENCE: 14
uauggcagga agaagcggat t                                                 21

<210> SEQ ID NO 15
<211> LENGTH: 21
<212> TYPE: RNA
<213> ORGANISM: Artificial Sequence
<220> FEATURE:
<223> OTHER INFORMATION: siRNA: N1400-1 (1)
<220> FEATURE:
<221> NAME/KEY: dTdT
<222> LOCATION: (20)..(21)

```
<400> SEQUENCE: 15
uauggcagga agaagcggat t                                              21

<210> SEQ ID NO 16
<211> LENGTH: 21
<212> TYPE: RNA
<213> ORGANISM: Artificial Sequence
<220> FEATURE:
<223> OTHER INFORMATION: siRNA: N1400-1 (2)
<220> FEATURE:
<221> NAME/KEY: dTdT
<222> LOCATION: (20)..(21)

<400> SEQUENCE: 16
uccgcuucuu ccugccauat t                                              21

<210> SEQ ID NO 17
<211> LENGTH: 21
<212> TYPE: RNA
<213> ORGANISM: Artificial Sequence
<220> FEATURE:
<223> OTHER INFORMATION: siRNA: N1402-3 (1)
<220> FEATURE:
<221> NAME/KEY: dTdT
<222> LOCATION: (20)..(21)

<400> SEQUENCE: 17
gaagcggaga cagcgacgat t                                              21

<210> SEQ ID NO 18
<211> LENGTH: 21
<212> TYPE: RNA
<213> ORGANISM: Artificial Sequence
<220> FEATURE:
<223> OTHER INFORMATION: siRNA: N1402-3 (2)
<220> FEATURE:
<221> NAME/KEY: dTdT
<222> LOCATION: (20)..(21)

<400> SEQUENCE: 18
ucgucgcugu cuccgcuuct t                                              21

<210> SEQ ID NO 19
<211> LENGTH: 73
<212> TYPE: RNA
<213> ORGANISM: Artificial Sequence
<220> FEATURE:
<223> OTHER INFORMATION: miR-30

<400> SEQUENCE: 19
cgcgacugua aacauccucg acuggaagcu gugaagccac gagauggcuu ucagucggau    60
guuugcagcu gcc                                                       73

<210> SEQ ID NO 20
<211> LENGTH: 71
<212> TYPE: RNA
<213> ORGANISM: Artificial Sequence
<220> FEATURE:
<223> OTHER INFORMATION: pSM2
<220> FEATURE:
<221> NAME/KEY: misc_feature
<222> LOCATION: (5)..(26)
<223> OTHER INFORMATION: n is a, c, g, or u
<220> FEATURE:
<221> NAME/KEY: misc_feature
<222> LOCATION: (46)..(67)
<223> OTHER INFORMATION: n is a, c, g, or u
```

```
<400> SEQUENCE: 20
cgcgnnnnnn nnnnnnnnnn nnnnnuagu gaagccacag auguannnnn nnnnnnnnnn      60
nnnnnnnugc c                                                          71
```

VECTOR, VECTOR COMBINATIONS, METHODS AND KIT THEREOF

TECHNICAL FIELD

The disclosure relates to a method of identification of antiviral molecules that help in efficient viral control and thereby aid in disease management. In particular, the disclosure relates to identification of anti-Tat molecules and hence is directed towards antiviral drug development. The disclosure also relates to Tat-inducible GFP-anti RFP shRNA vector, vector combinations, recombinant cell having instant vectors, methods and kits thereof.

BACKGROUND AND PRIOR ART

Historically, several approaches have been employed to control the proliferation and infectivity of HIV by identifying various targets that are crucial for the virus to bring about the infection. In the present scenario the following types of antiviral therapies are commonly known.

a. Anti-Retroviral Therapy Efficiently Controls Viral Proliferation: As a consequence of rapid regeneration rate and high magnitude genetic variation, HIV can rapidly develop drug resistance. To minimize and/or prevent the emergence of drug resistance, anti-retroviral therapy (ART) is typically administered as multi-drug therapy consisting of a minimum of three different drugs often targeting more than one viral factor. The primary objective of ART is to control viral proliferation but not viral eradication. Combination therapy that is administration of three or more drugs is also called highly active antiretroviral therapy (HAART). The viral enzymes reverse transcriptase (RT) and protease are the most common targets for the ART. The anti-RT drugs essentially fall under two classes (1) Nucleoside/Nucleotide Reverse Transcriptase Inhibitors (NRTIs) and (2) Non-NRTIs (NNRTIs). In the developing countries, HAART consists of combinations of these two anti-RT classes only as they are economically affordable. For more efficient viral control, protease inhibitors (PIs) are also included in the HAART especially in the developed countries. In addition to the above classes, drugs targeting other viral factors or stages are also in use including entry inhibitors, fusion inhibitors and a single integrase inhibitor. Today approximately 25 anti-retroviral inhibitors falling under one of the above classes have been licensed by the Food and Drug Administration for clinical use. Many more new drugs under the above classes or novel classes are at various levels of clinical evaluation (Example: drugs targeting viral maturation or viral factor Tat). In the absence of a promising preventive vaccine, today ART is the only medical intervention strategy for efficient disease management.

b. Anti-Retroviral Therapy Must Target Multiple Viral Factors: To prevent emergence of drug resistance, multiple viral factors must be targeted since the virus cannot generate multiple mutations and yet remain fit. For socio-economic and technical reasons, anti-RT and protease inhibitors constitute the most commonly used HAART regimens. These drugs could also antagonize the various host cellular polymerases and proteases thus manifesting severe side effects often leading to non-compliance which in turn results in drug resistance. Drug resistance to one specific inhibitor could make the virus resistant to all the other members under the same class thus significantly curtailing the options available to the clinician. When drug resistance emerges against the 'first line therapy, a 'second line therapy', consisting of drugs at least from one new class, is usually recommended. Second line therapy inhibitors are, however, expensive and beyond the reach of many subjects especially in developing countries. Switching to second line therapy is also necessitated for drug toxicity reasons.

c. Tat Offers a Good Target for Anti-Viral Inhibitors: Most of the small molecule drugs are likely to possess toxic side effects that differ only in the magnitude of severity. However, drugs that target viral enzymes (polymerases or proteases) are more likely to be toxic since they antagonize host cellular enzymes to variable extent. One possible solution is to target viral factors like Tat that do not have perfect match in the host system, unlike RT and protease. Small molecule inhibitors (SMI) to Tat are less likely to be toxic in comparison to those targeting viral enzymes for specificity reasons. Tat is a viral transactivator that controls gene expression regulation from the viral promoter, the long-terminal repeat (LTR). Although the LTR is functional in the absence of Tat, especially soon after viral infection where Tat is yet to be made, under the influence of Tat, the LTR is one of the strongest mammalian promoters known often up-regulating gene expression 100-1000 fold. Tat also constitutes an important molecular switch between active viral proliferation and viral latency. Absence of Tat in the cell pushes the virus into a genetically silent mode called viral latency. A latent viral infection is recalcitrant to retroviral therapy and immune response thus posing a serious challenge to viral eradication efforts. Given that no host equivalent of Tat exists in the cell and that Tat plays an important role in viral gene expression and establishment and maintenance of viral latency, developing SMI to Tat is extremely important. Additionally, inhibiting Tat broadens the range of ART by adding a novel viral target thus minimizing the emergence of drug resistance.

d. Small Molecule Inhibitors to Tat are not Available: Of the various kinds of Tat inhibitors, including siRNA, intrabodies, aptamers etc, only small molecule inhibitors (SMI) have a potential of practical application to the clinic. SMI have the following advantages (1) unlike other inhibitors, chemical libraries consisting of a very wide range of molecules are available for SMI, (2) furthermore, SMI have a superior reach in that small molecules can reach each and every infected cell in the body, (3) additionally, SMI have an advantage of economically low cost but large scale synthesis. Despite all the merits, paradoxically, no anti-Tat SMI are available today. Worse, there are no drugs at any level of clinical trial targeting Tat. In the 1990s a few pharmaceutical companies identified a few molecules with anti-Tat properties but for unknown reasons, these molecules did not progress to clinical trials. Ro 24-7429, the Hoffmann-La Roche is one such example. There have been several reports on anti-Tat inhibitors in the medical literature; however, none of them reached an advanced stage of pharmaceutical development. Despite thousands of scientific publications on the HIV Tat, the knowledge is not translated into practical drug development.

e. Limitation of the Existing HTS (High Throughput Screening) Assays: Tat is a viral transactivator that controls gene expression from its own promoter, the viral LTR. In the presence of Tat, the LTR makes 100 to 1000 times more viral protein for instance. Tat also controls establishment and maintenance of viral latency. The property of gene expression control of the viral LTR is exploited to develop the standard HTS assay for Tat regardless the nature of the inhibitor. Typically, a reporter gene like green fluorescent protein (GFP) is placed under the control of HIV-1 LTR on a DNA plasmid. Mammalian cells with stably integrated LTR-GFP plasmid could be established and such are called reporter cell lines. Reporter cell lines express GFP in the presence of Tat (FIG. 1) and if Tat is blocked expression of GFP is also inhibited. A Tat-inducible GFP expressing cell line could used in a high throughput screening (HTS) to screen for molecules that may possess anti-Tat or anti-HIV properties.

The most serious limitation of the standard reporter cell lines is that they cannot discriminate between cytotoxic molecules and anti-viral compounds since in both of these events GFP is likely to be down regulated (FIG. 2). For instance, an SMI that interferes with the regular process of cellular protein synthesis could results in the down regulation of GFP expression but not due to anti-viral property. Such a molecule also will be cytotoxic resulting in cell death or tissue injury. Given the complexity of the cellular metabolism, any SMI that interferes with any of the essential biochemical pathways is likely to be cytotoxic and often may lead to GFP down-regulation offering false hits. Such molecules will be proved unsuccessful after enormous effort of characterizing them. This is one reason why most of the drug screen assays failed to identify SMI that are non-cytotoxic and anti-viral for HIV and Tat.

In the absence of a preventive vaccine, chemotherapy is the only available option today for effective disease management for HIV/AIDS. HIV has a potential for generating extraordinarily great levels of genetic variation that leads to rapid drug resistance. Furthermore, the most commonly used anti-viral drugs are highly toxic given that these drugs primarily target viral polymerase and protease, the enzymes that have host equivalents. Additionally, development of drug resistance to one specific drug could lead to broad-level resistance to the entire class thus making any other drug under the same class ineffective. It is therefore critical to identify drugs to counter viral drug resistance. Importantly, the drugs must target less commonly employed viral targets to widen the effectiveness of the anti-retroviral therapy. To this end, targeting viral factors is less likely to be toxic given the absence of host homologues of these viral factors. Despite these merits, essentially there have been no anti-viral factor drugs approved by FDA today in the market, except reltegravir. The traditional method of structure-based-drug-design has not been applicable to some viral factors given that the crystal structure of the factors could not be determined owing to its structural flexibility. Several of these drugs are at various levels of evaluation in clinical trials and none yet reached the clinic. The present disclosure presents aspects which overcome the demerits observed in the prior research in this field of technology.

STATEMENT OF THE DISCLOSURE

Accordingly, the present disclosure relates to a vector comprising nucleotide sequence set forth as Seq ID No. 1 or Seq ID No. 2; a method of obtaining vector comprising nucleotide sequence set forth as Seq ID No. 1 or Seq ID No. 2, said method comprising acts of: a) obtaining expression vector set forth as Seq ID No. 3, and b) inserting heterologous element and Long Terminal Repeat [LTR] sequence into the expression vector to obtain the vector comprising nucleotide sequence set forth as Seq ID No. 1 or Seq ID No. 2; a vector combination consisting vectors selected from a group comprising nucleotide sequence set forth as Seq ID No. 1 or Seq ID No. 2 or a combination thereof along with: a) Reporter Protein expression vector, or b) Tat expression vector or any combination thereof; a recombinant cell comprising: a) vector comprising nucleotide sequence set forth as Seq ID No. 1, or b) vector comprising nucleotide sequence set forth as Seq ID No. 2, or c) vector of step (a) along with reporter protein expression vector or tat expression vector or any combination thereof, or d) vector of step (b) along with reporter protein expression vector or tat expression vector or any combination thereof, or any combination thereof; a method of obtaining recombinant cell as mentioned above, said method comprising acts of: a) obtaining vector comprising nucleotide sequence set forth as Seq ID No. 1 or Seq ID No. 2, b) optionally combining the vector of step (a) or both the vectors of step (a) along with Reporter Protein expression vector or Tat expression vector or any combination thereof, and c) transfecting a host cell with the vector vector of step (a) or both the vectors of step (a) or combination of step (b) to obtain the recombinant cell; a method of identifying and optionally quantifying viral inhibitor molecule, said method comprising acts of: a) obtaining vector comprising nucleotide sequence set forth as Seq ID No. 1 or Seq ID No. 2, b) optionally combining the vector of step (a) or both the vectors of step (a) along with Reporter Protein expression vector or Tat expression vector or any combination thereof, c) transfecting a host cell with the vector vector of step (a) or both the vectors of step (a) or combination of step (b) to obtain a recombinant cell, and d) adding inhibitor molecule to the recombinant cell and screening for identifying and optionally quantifying the viral inhibitor molecule; a kit for identifying and optionally quantifying viral inhibitor molecule or inhibiting Tat, said kit comprising components selected from group having vector as mentioned above, vector combination as mentioned above, cell as mentioned above, Reporter Protein expression vector, Tat expression vector, expression vector set forth as Seq ID No. 3, inhibitor molecule and instruction manual or any combination thereof and a method of assembling a kit for identifying and optionally quantifying viral inhibitor molecule or inhibiting Tat, said method comprising act of combining components selected from group comprising vector as mentioned above, vector combination as mentioned above, cell as mentioned above, Reporter Protein expression vector, Tat expression vector, expression vector set forth as Seq ID No. 3, inhibitor molecule and instruction manual or any combination thereof.

BRIEF DESCRIPTION OF THE ACCOMPANYING FIGURES

The patent or application file contains at least one drawing executed in color. Copies of this patent or patent application publication with color drawings will be provided by the Office upon request and payment of the necessary fee. In order that the disclosure may be readily understood and put into practical effect, reference will now be made to exemplary embodiments as illustrated with reference to the accompanying figures. The figure together with a detailed description below, are incorporated in and form part of the specification, and serve to further illustrate the embodiments and explain various principles and advantages, in accordance with the present disclosure where:

Figure 4:
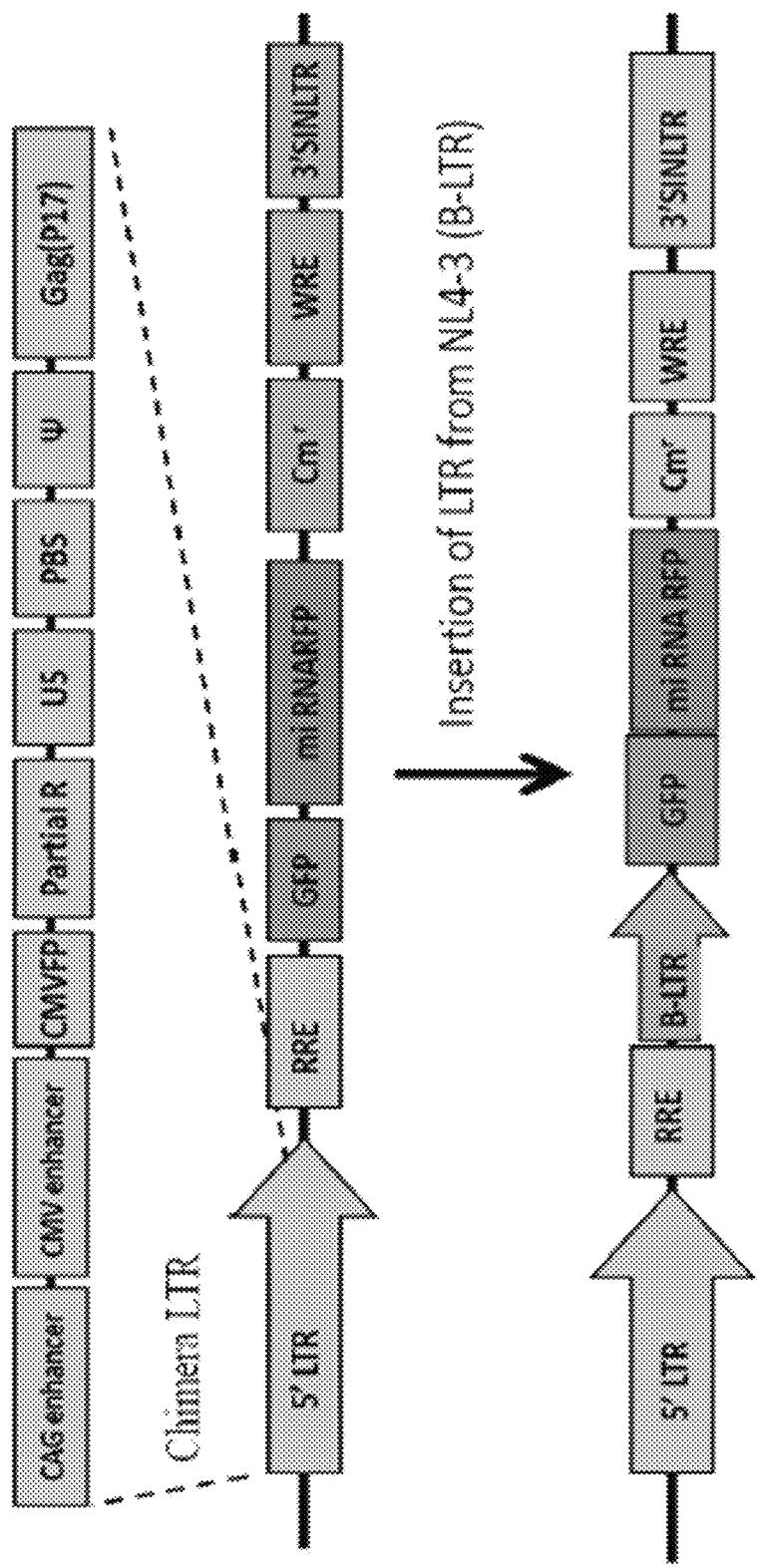

FIG. 4 shows the top panel which depicts the schematic diagram of the original vector. Expression of GFP and anti-RFP shRNA (blue box) is controlled by a chimera LTR. In the bottom panel, a different LTR is inserted so that expression of these two genes is transferred to the new viral promoter which became now Tat-responsive unlike in the original vector.

Figure 5:
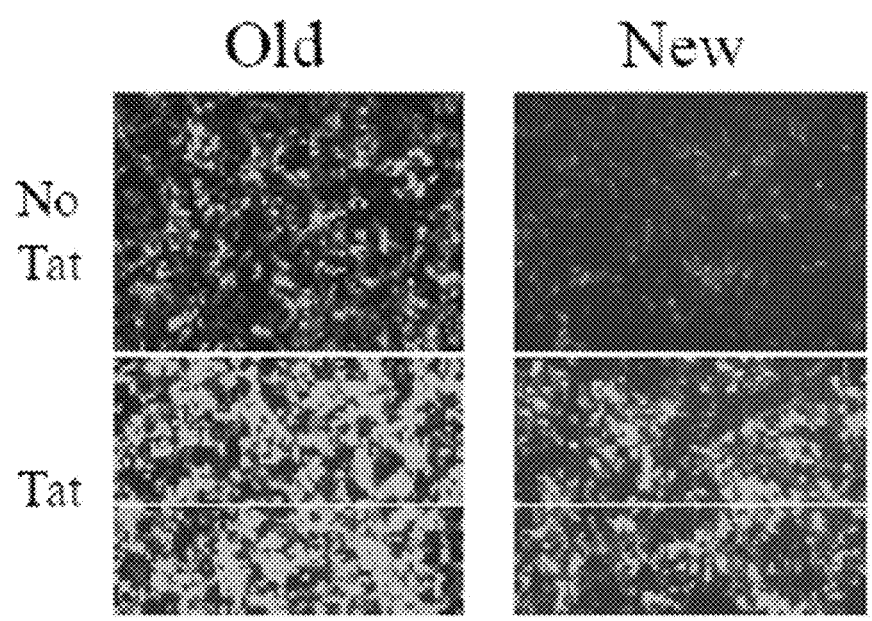

FIG. 5 shows the original (old) vector shows high level GFP expression in the absence of Tat. Background GFP expression problem is minimized in the new vector.

Figure 1:
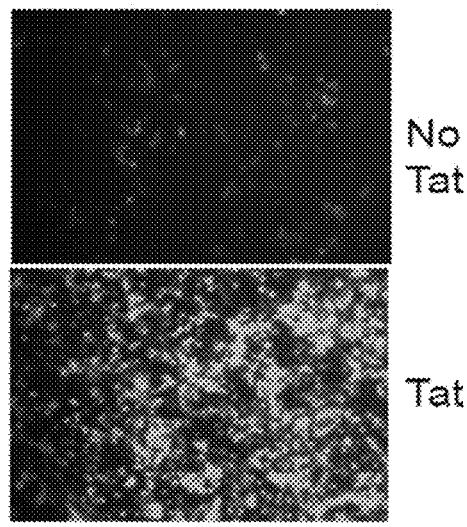
FIG. 1 shows that the expression of GFP is up-regulated in the presence of Tat in HEK293 cells.
Figure 2:
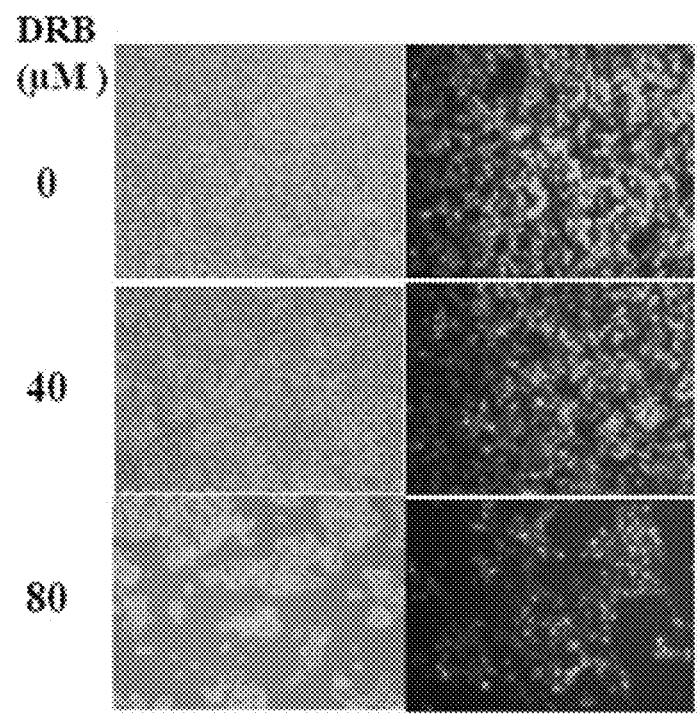
FIG. 2 shows enhanced cell death with increasing concentrations of DRB, a small molecule inhibitor of CDK9, an essential cellular enzyme. GFP expression also is reduced when the drug concentration increased although the drug is not expected to have a direct effect on Tat.
Figure 6:
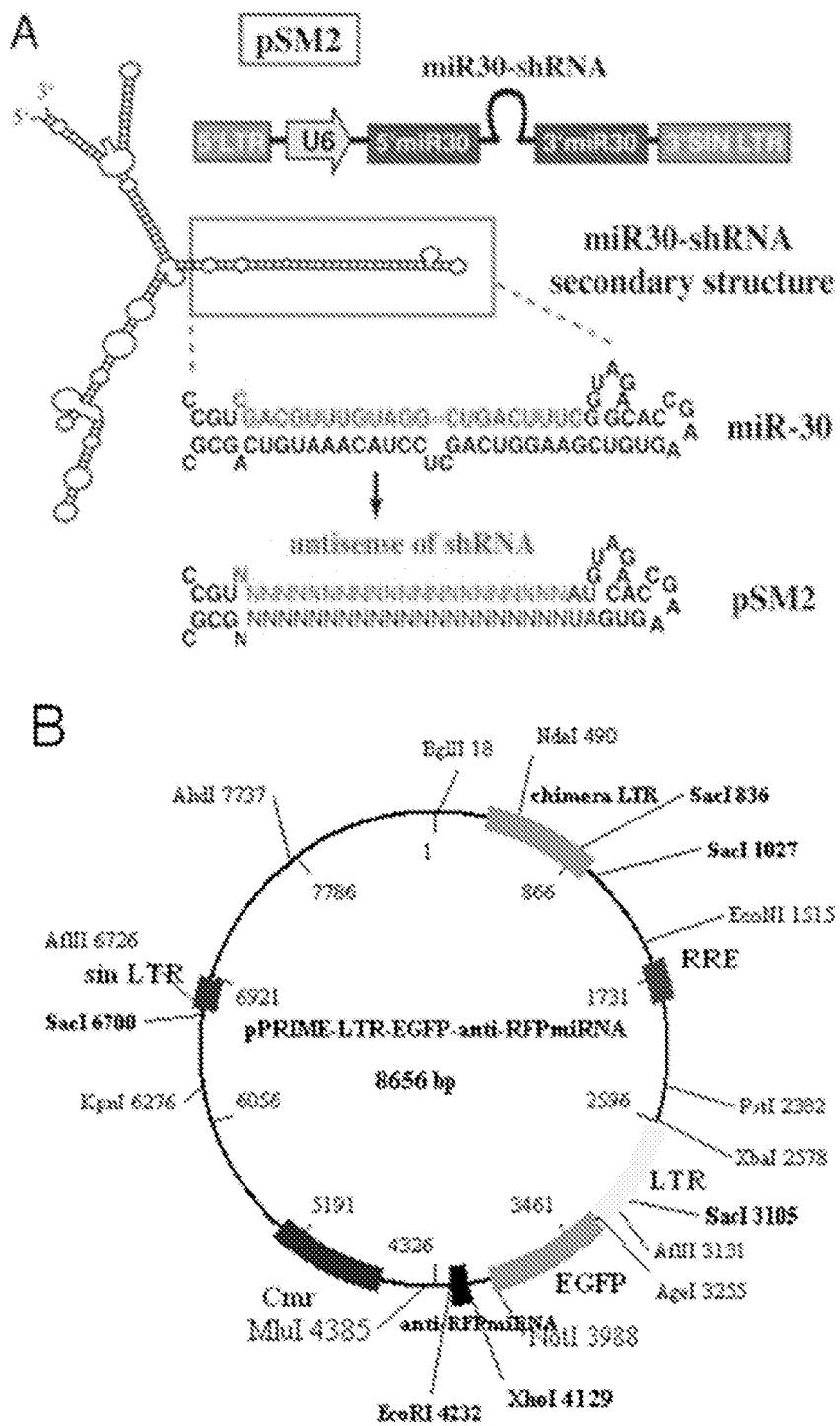

FIG. 6 shows (A) The miRNA vector structure as in Stegmeier F et al PNAS, 13212-7, 2005 (see Fig. 1 in that publication). Note that instead of the yellow box 'U6', the version of the vector used contains the organization as depicted in Fig. 4 above. The sequences of the hairpin loop (highlighted using a box) shown in red color (SEQ ID NO:20 for pSM2) are the ones replaced by the anti-RFP shRNA sequences (as shown in Table-1; SEQ ID NO:19 shown from miR-30 in the FIG.). To these sequences in the table, the loop sequences as shown in the figure and appropriate anti-sense sequences (N sequences in black) are added. The whole sequence is cloned into appropriate restriction enzyme sites (located at the base of the loop (not shown). The miRNA is processed by the cellular machinery to release the shRNA embedded which binds the target mRNA (RFP in the present context) and causes its destruction. (B) The schematic diagram of the parental vector map into which the anti-RFP shRNA sequences are cloned between XhoI and EcoRI sites.

Figure 7:
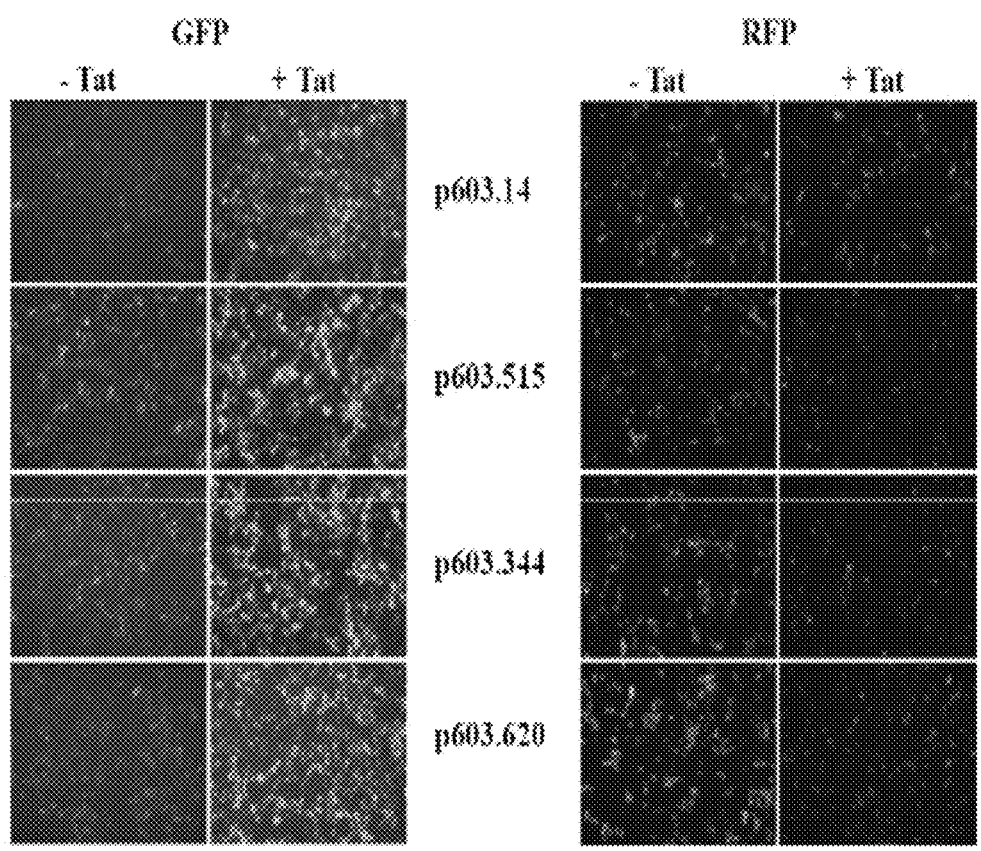

FIG. 7 shows that four different anti-RFP shRNA vectors tested individually in HEK293 cells for their RNA inhibition property in the presence of Tat. Cells are transfected with a vector combination of '2' as in Table-2. With the exception of 603.14, all the other three shRNAs down-regulate RFP expression significantly. Images are taken at 48 h.

Figure 8:
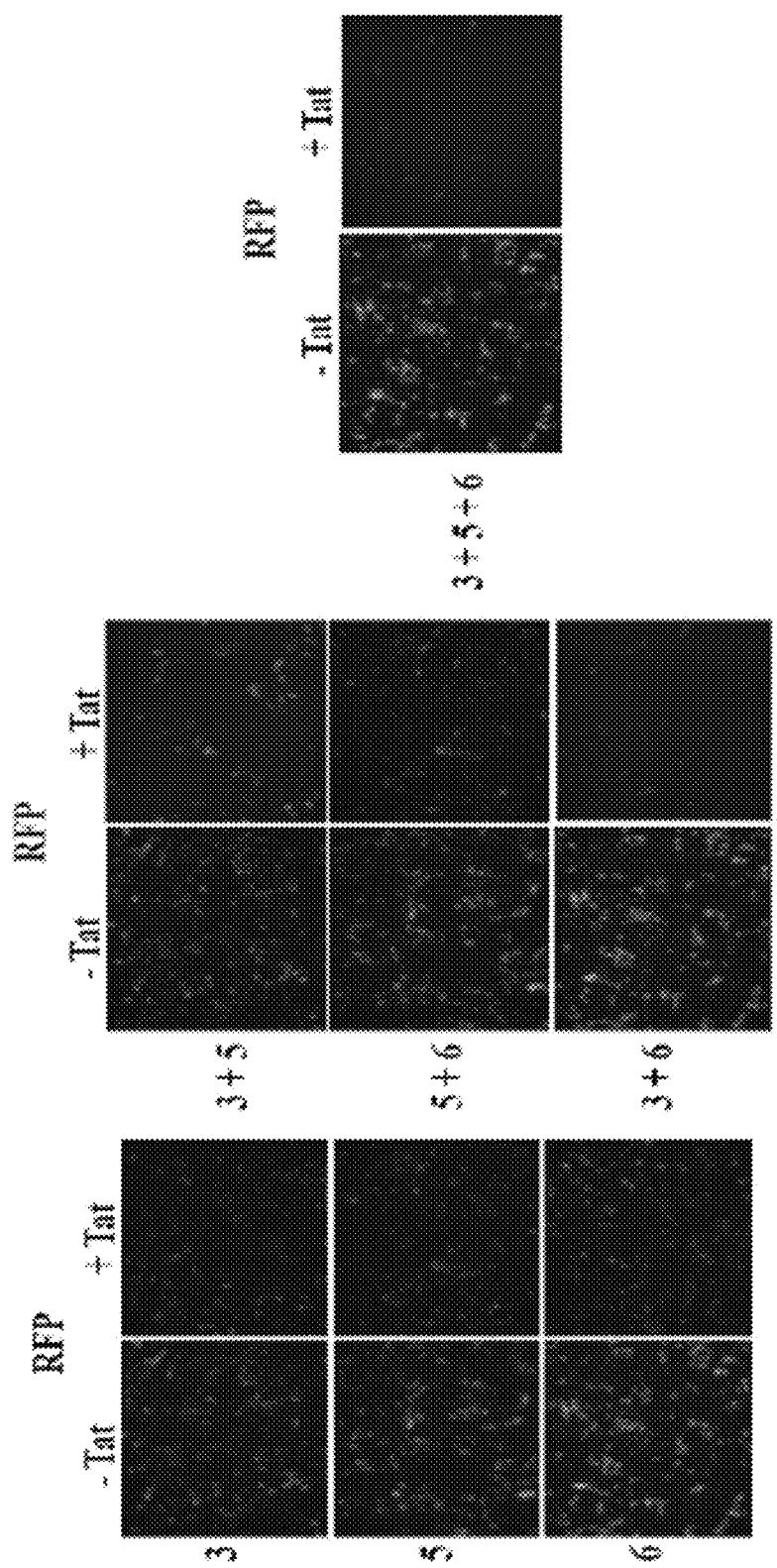

FIG. 8 shows that combinations of the three different anti-RFP shRNA are tested for synergistic effect in suppressing RFP in HEK 293 cells. The numbers 3, 5 and 6 represent shRNAs 603.344, 603.515 and 603.620, respectively. Each shRNA individually suppressed RFP with good efficiency. However, the combination of 3 and 6 appears to display the best and maximum suppression. The combination of these two shRNA is used in subsequent experiments. Images are taken at 48 h.

Figure 9:
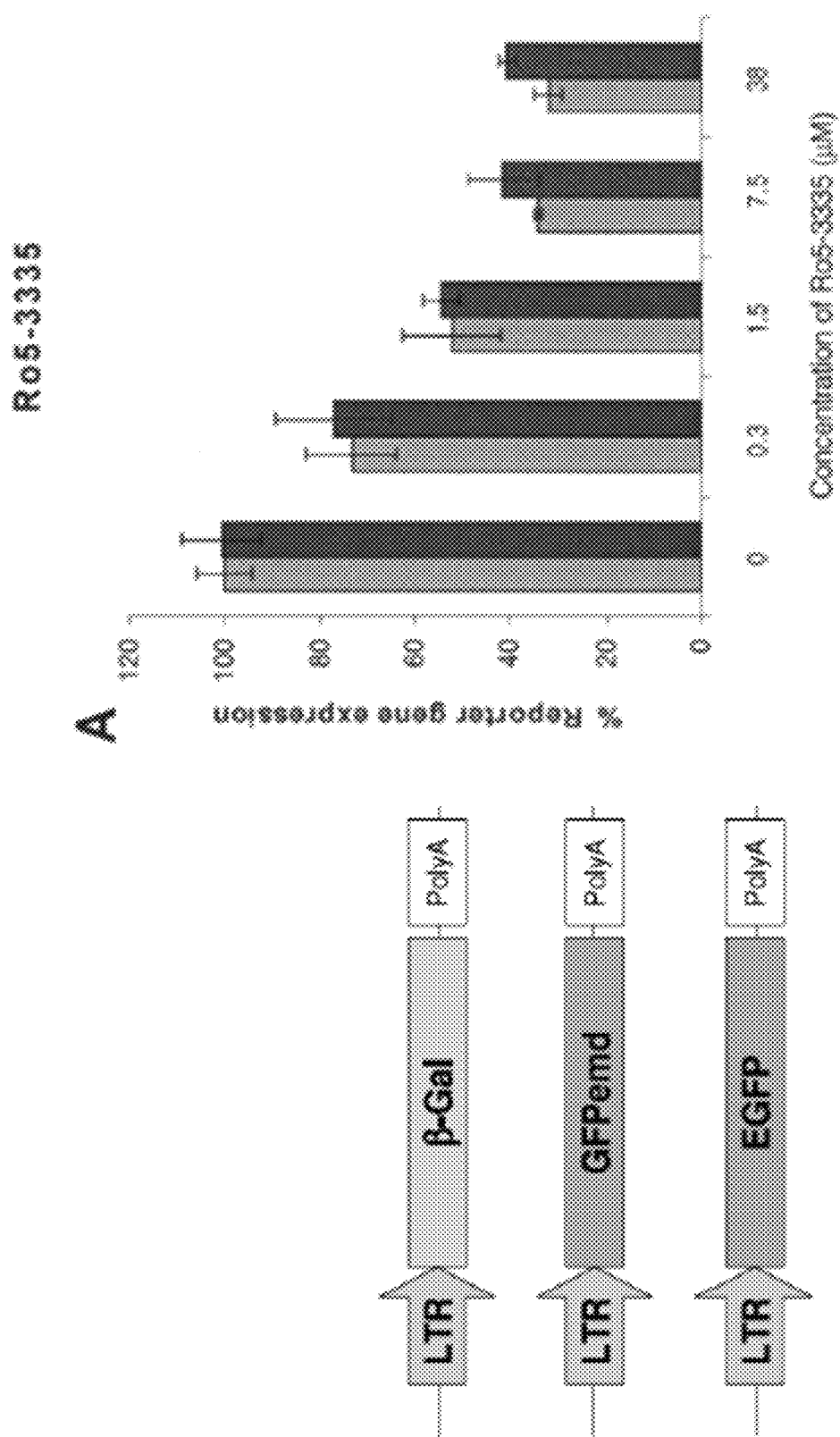

FIG. 9 shows the left panel which depicts the design of reporter gene expression vectors under the control of the viral promoter, the LTR. The right hand panel shows how GFP expression is down-regulated in HeLa cells with increasing concentration of a known small molecule inhibitor R05-3335 (data from FIG. 4, Daelemans D et al).

Figure 10:
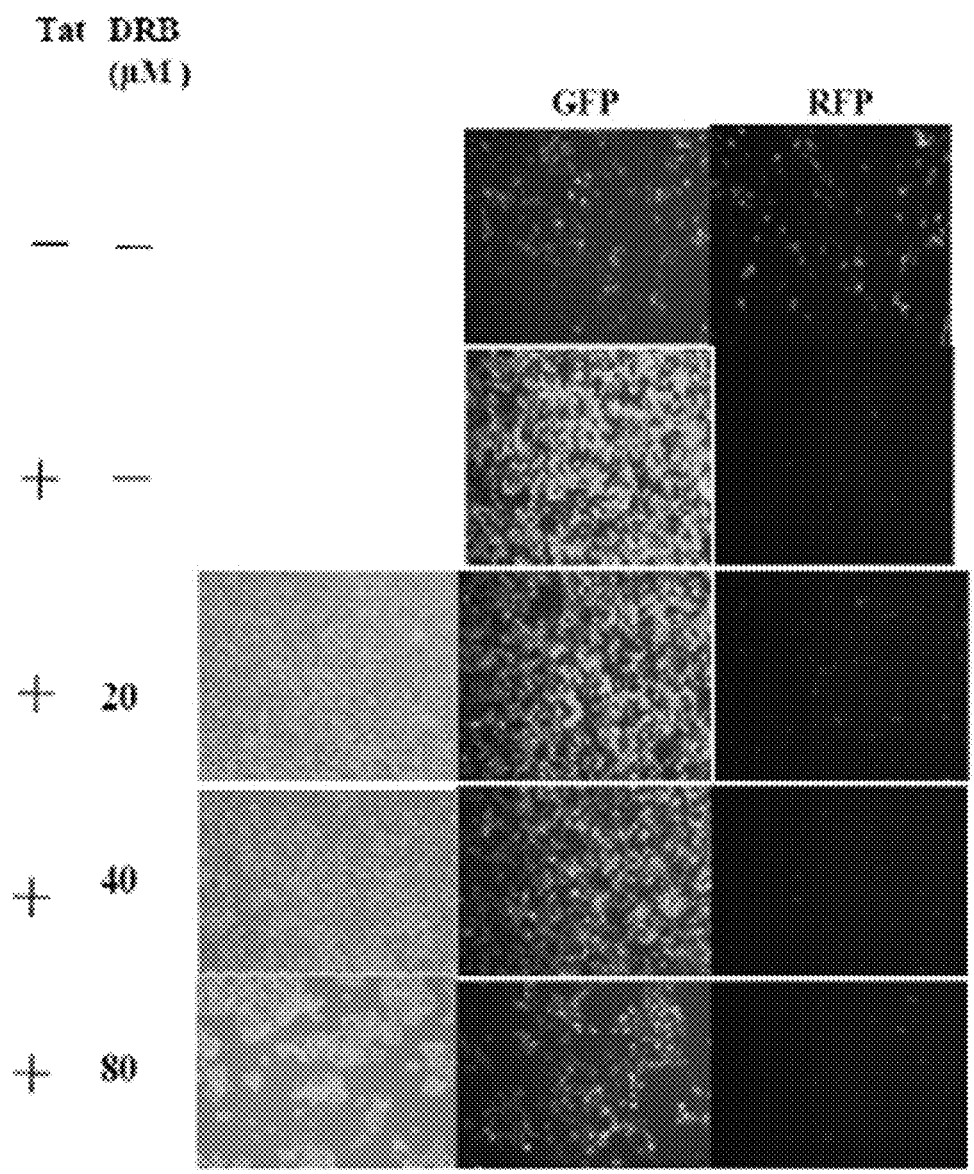

FIG. 10 shows that the experiment is done in HEK 293 cells using plasmid combinations as delineated in Table-2. Tat up-regulates GFP expression (middle panels). But, in the presence of DRB, there is a progressive reduction in GFP expression as the drug concentration increased. On the left hand side, light microscopy photos of the same cells show increasing levels of cytotoxicity. If DRB is really a Tat inhibitor, RFP expression should have been up-regulated, which is not the case here. Thus, a cytotoxic molecule down-regulates GFP without being a Tat inhibitor.

Figure 11:
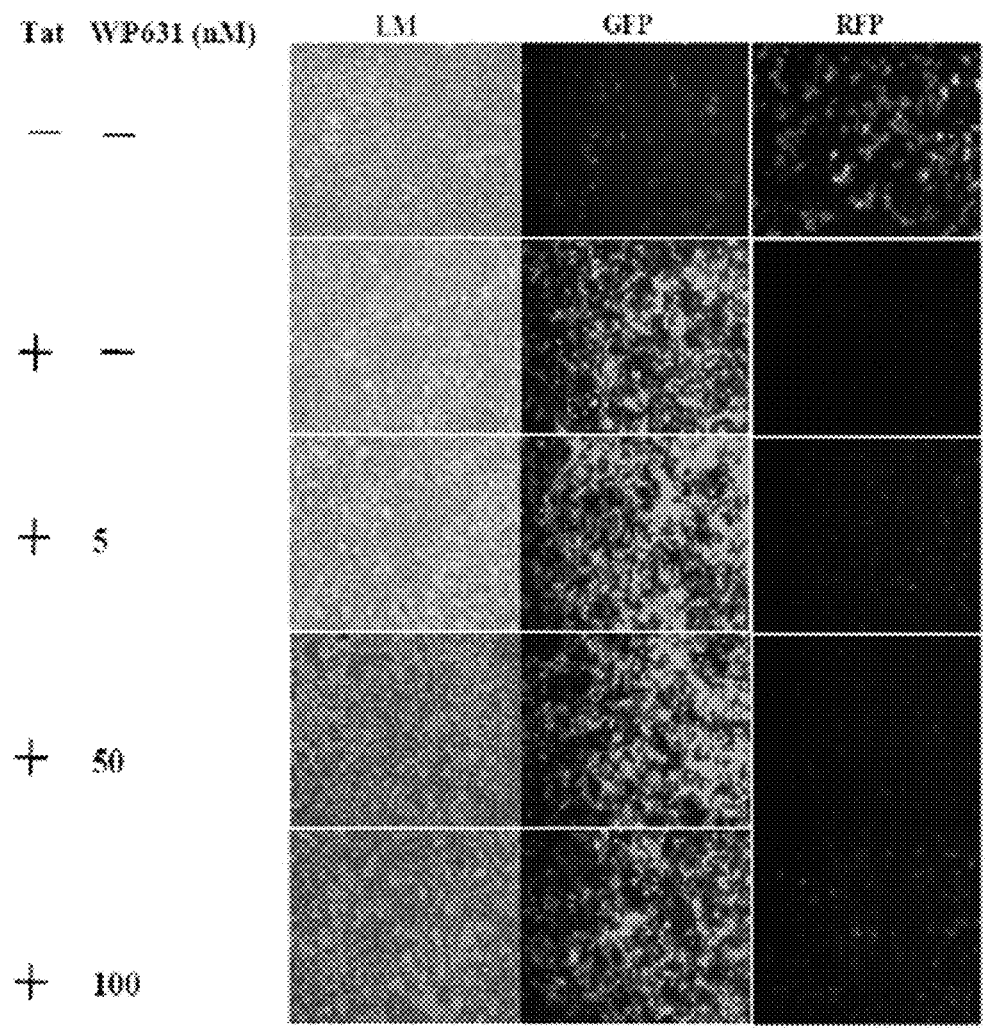

FIG. 11 shows small molecule inhibitor WP631, anti-Sp1, causes apoptosis at higher concentrations and marginal down regulation of GFP and insignificant levels of up-regulation of RFP.

Figure 12:
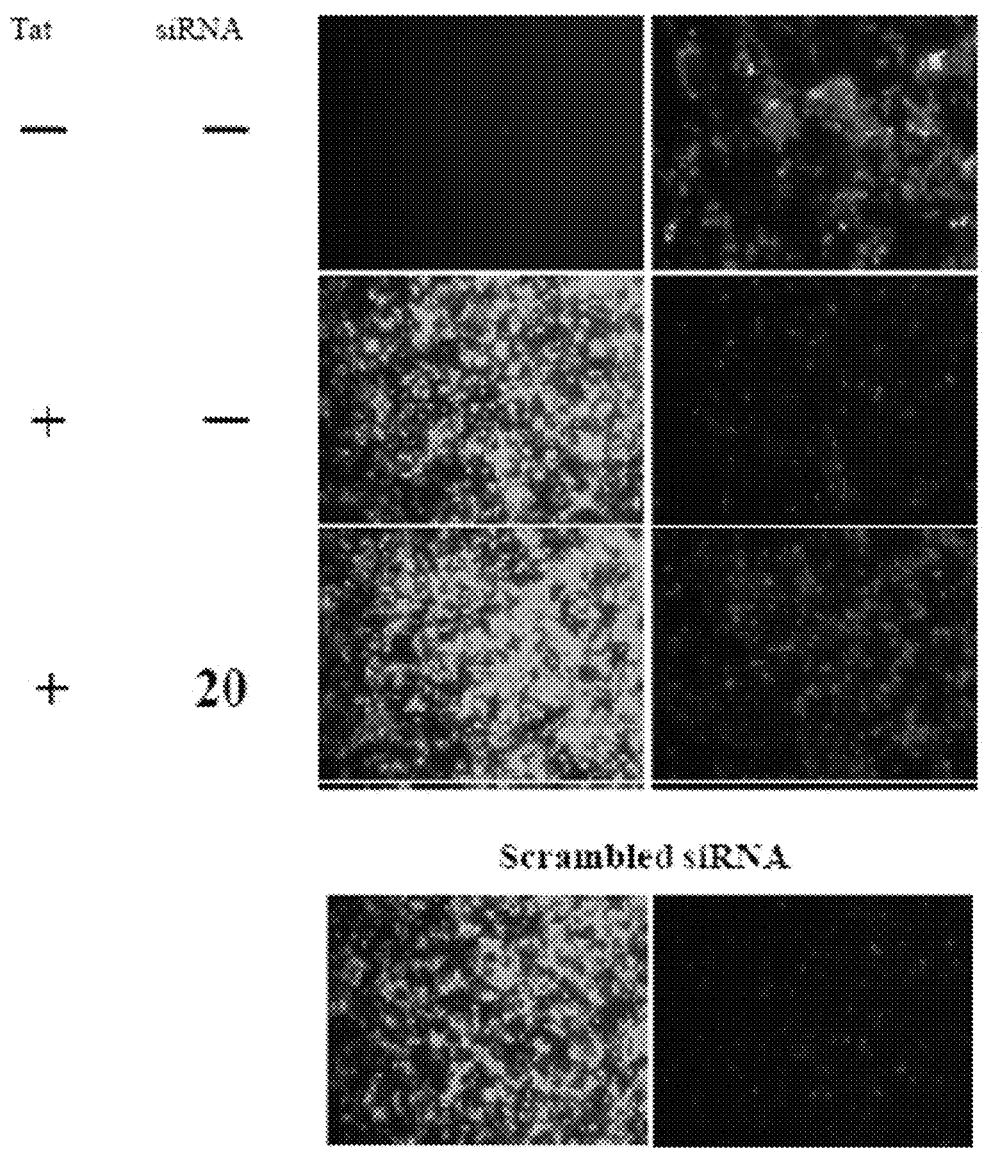

FIG. 12 shows that anti-Tat siRNA restores RFP expression. 293 cells are transiently transfected with or without specified quantity of anti-Tat siRNA (nM). The cells also received all the three other vectors (Tat, RFP and anti-RFP shRNA expression vectors). Scrambled RNA expression control does not upregulate RFP as expected.

Figure 13:
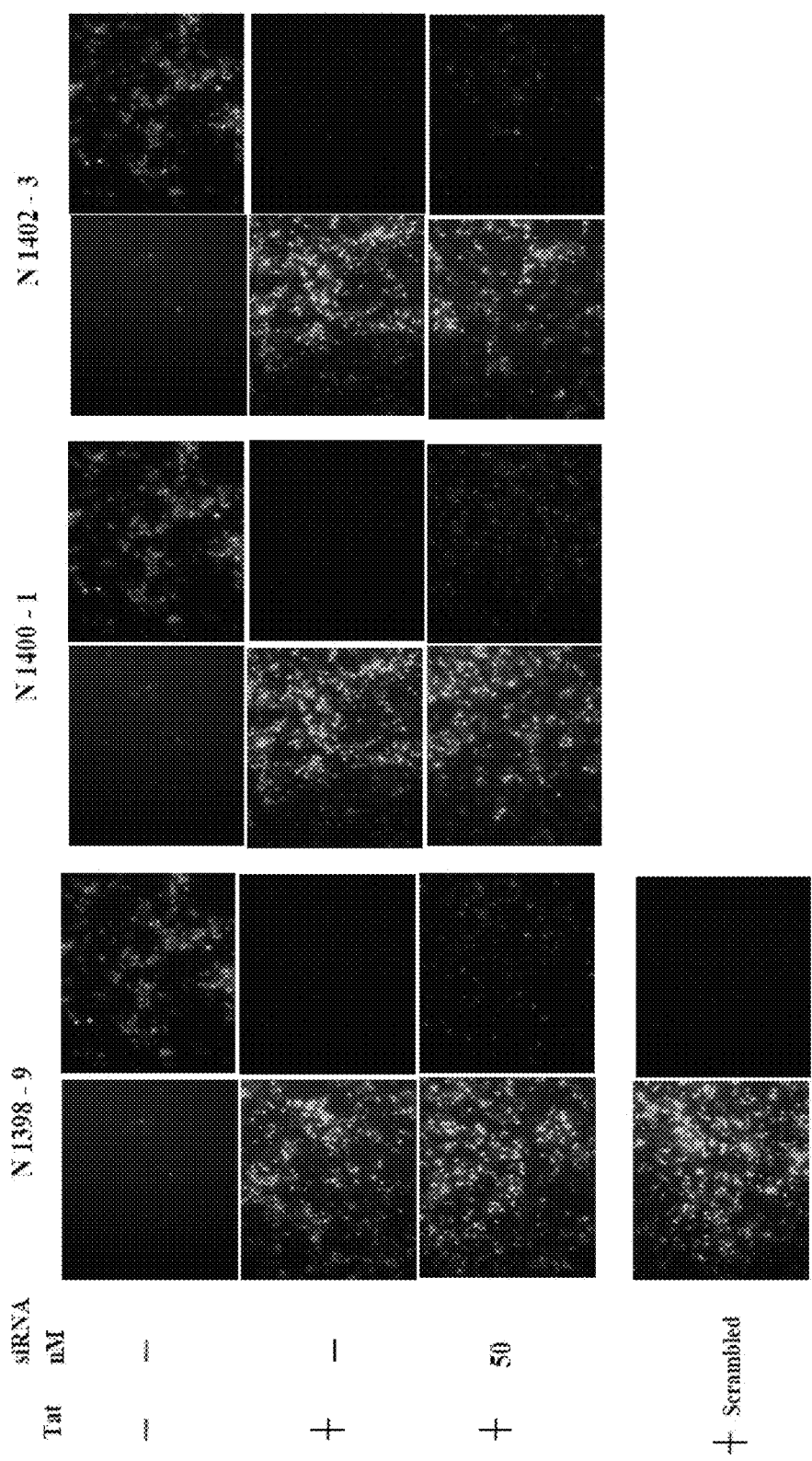

FIG. 13 shows Anti-Tat activity of three different siRNA molecules. 293 cells are transiently transfected with pPRIME-LTR-GFP: anti-RFP miRNA (p604.344 and p604.620), CMV-RFP and CMV-Tat (YU-2) vectors. Cells are transfected with one of the anti-Tat siRNA molecules. GFP and RFP expression is recorded 48 h after vector transfection. Scrambled siRNA is used as a negative control.

Figure 14:
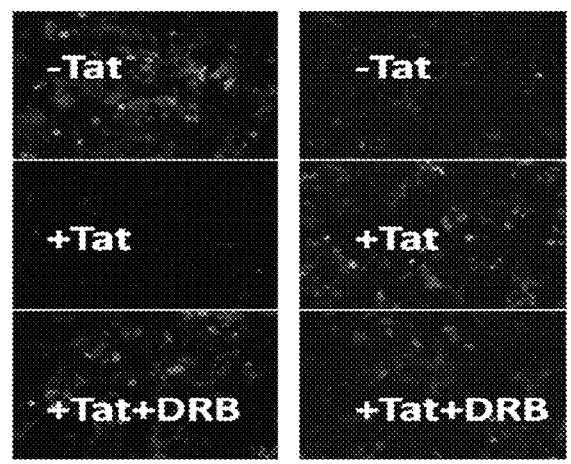

FIG. 14 shows DRB relieves RFP gene expression. HeLa cells are transiently transfected with pPRIME-LTR-GFP: anti-RFP miRNA (p604.344 and p604.620), CMV-RFP and EF-1α-Tat (YU-2) vectors. Cells are treated with 25 μM DRB. GFP and RFP expression is recorded 24 h after vector transfection.

Figure 15:
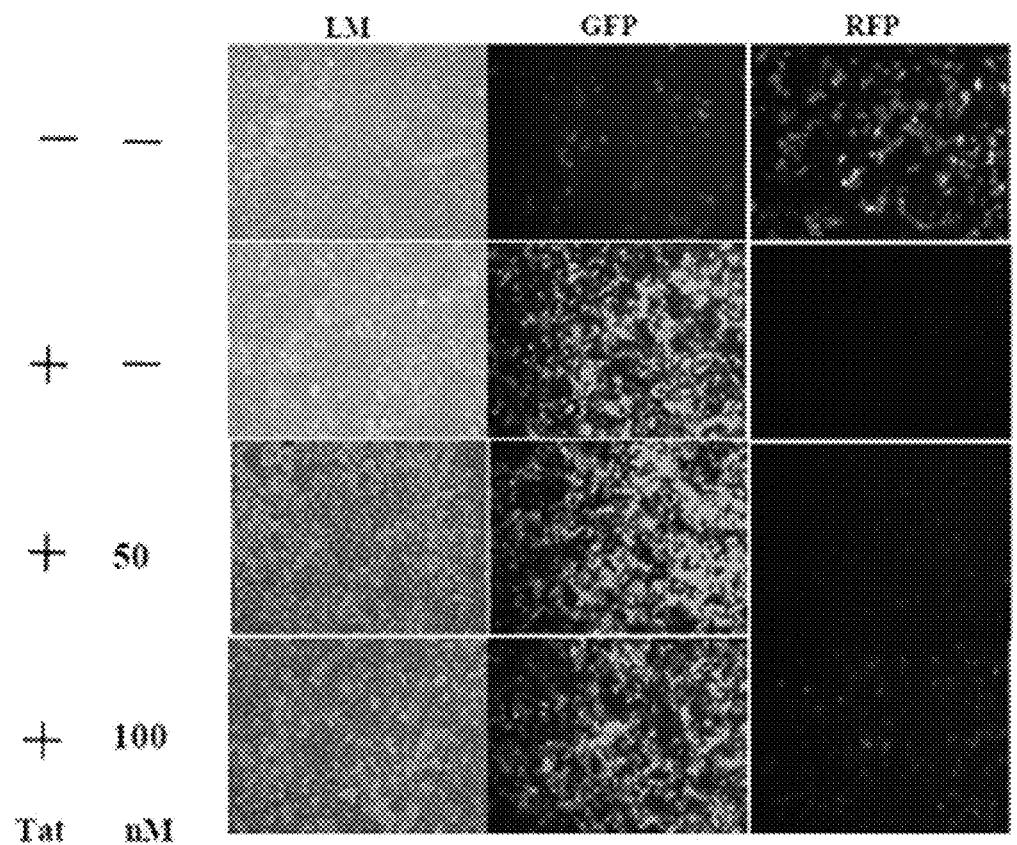

FIG. 15 shows WP631 partially relieves RFP gene expression. 293 cells are transiently transfected with pPRIME-LTR-GFP: anti-RFP miRNA (p604.344 and p604.620), CMV-RFP and EF-1α-Tat (YU-2) vectors. Cells are treated with different concentrations of the SMI 24 h after transfection. GFP and RFP expression is recorded 24 h after vector transfection. LM, Light microscopy.

Figure 16:
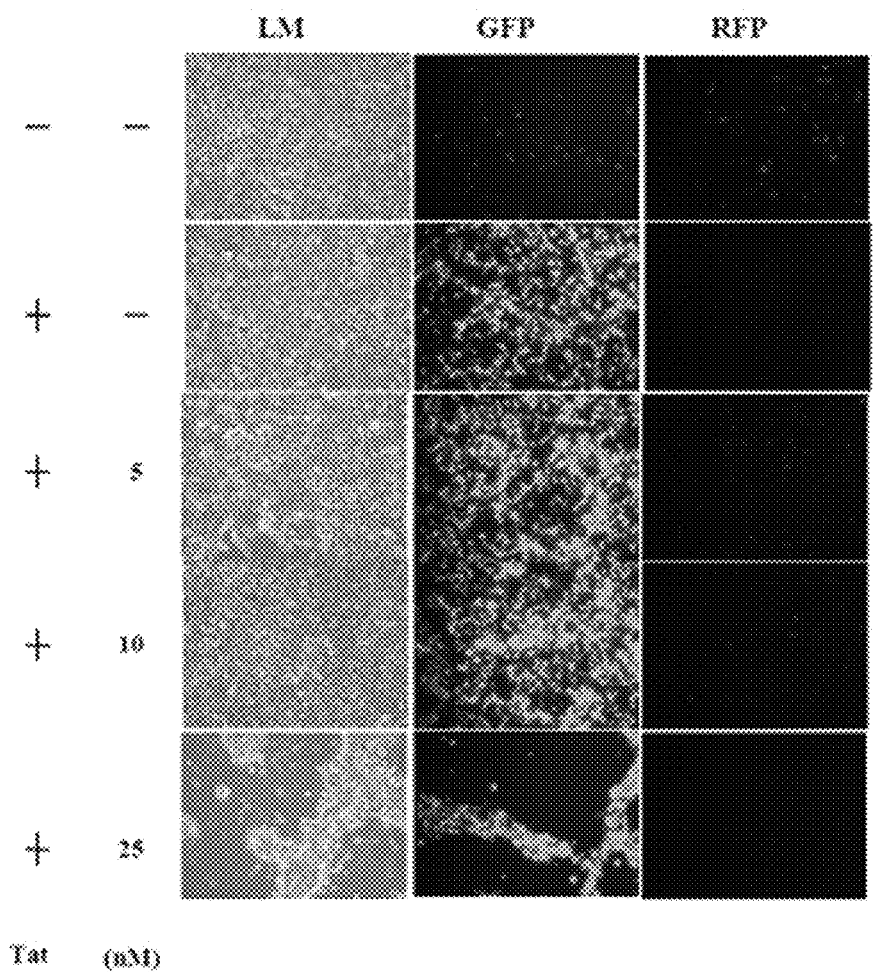

FIG. 16 shows Anti-Tat activity of flavopiridol. 293 cells are transiently transfected with pPRIME-LTR-GFP: anti-RFP miRNA (p604.344 and p604.620), CMV-RFP and CMV-Tat (YU-2). Cells are treated with different concentrations of flavipiridol which is an inhibitor of cellular CDK. GFP and RFP expression is recorded 48 h after vector transfection.

Figure 17:
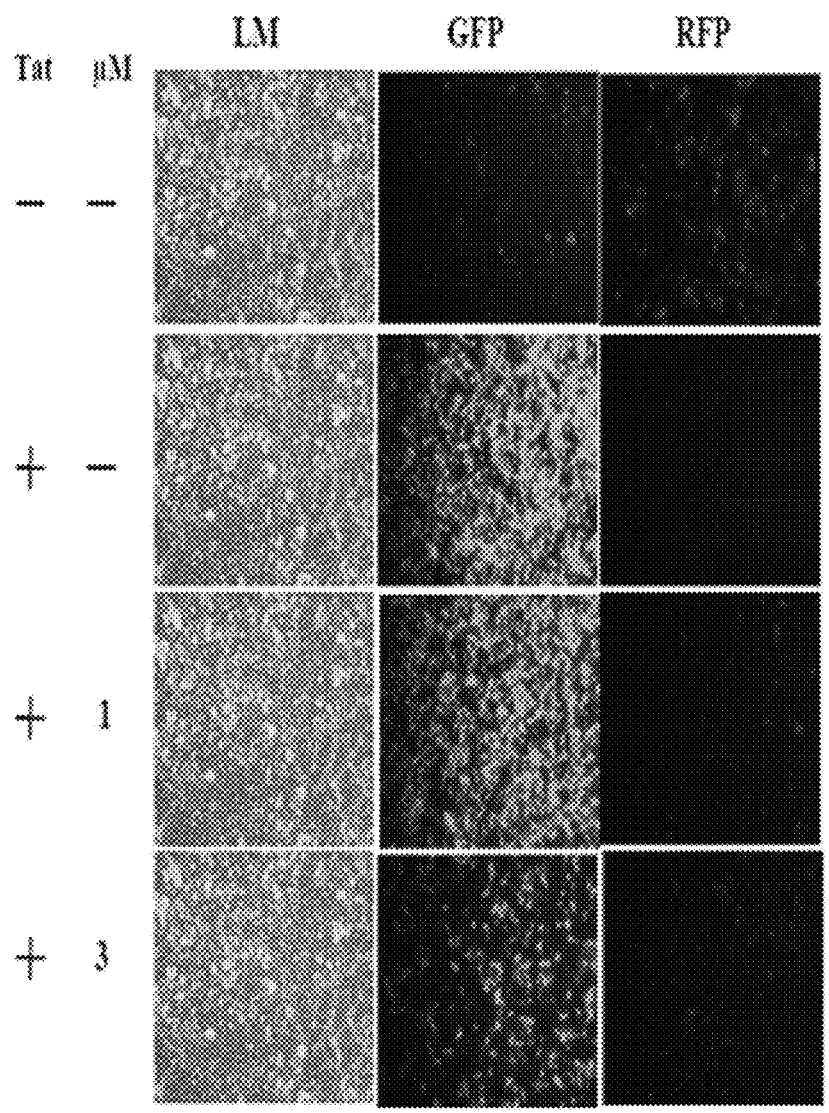

FIG. 17 shows Anti-Tat activity of roscovitine. 293 cells are transiently transfected with pPRIME-LTR-GFP: anti-RFP miRNA (p604.344 and p604.620), CMV-RFP and CMV-Tat (YU-2). Cells are treated with different concentrations of roscovotine which is an inhibitor of cellular CDK. GFP and RFP expression was recorded 48 h after vector transfection.

Figure 18:
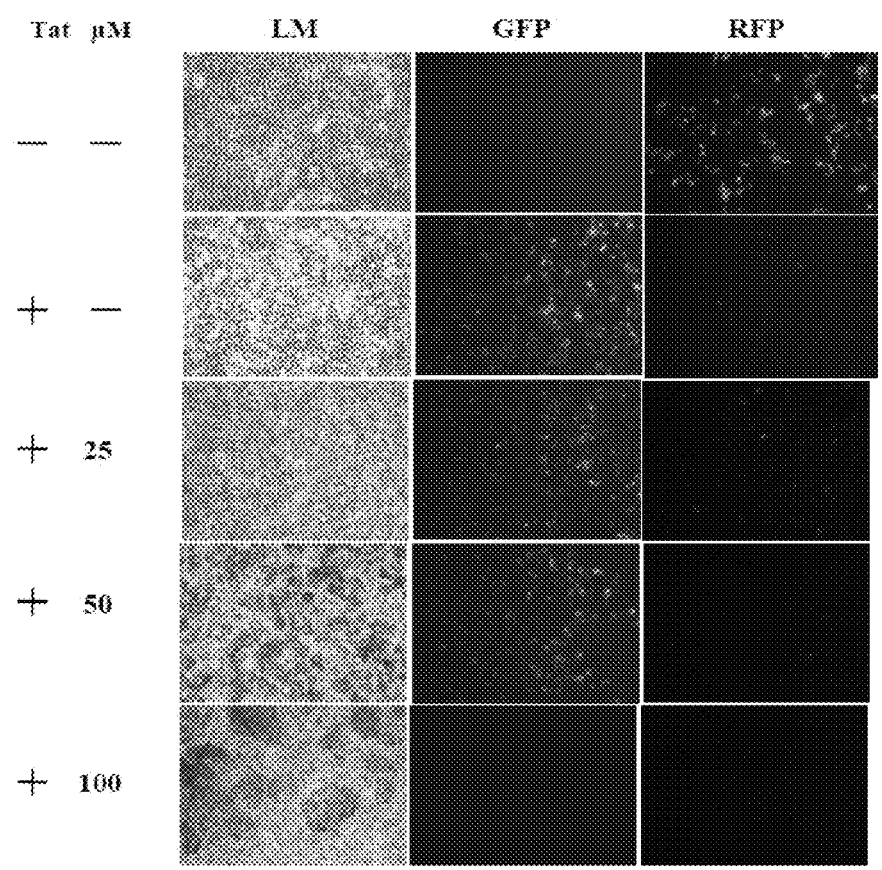

FIG. 18 shows Anti-Tat activity of LTK14. 293 cells were transiently transfected with pPRIME-LTR-GFP: anti-RFP miRNA (p604.344 and p604.620), CMV-RFP and CMV-Tat (YU-2). Cells were treated with different concentrations of LTK14 which is an inhibitor of cellular histone acetyl transferases. GFP and RFP expression was recorded 48 h after vector transfection.

Figure 19:
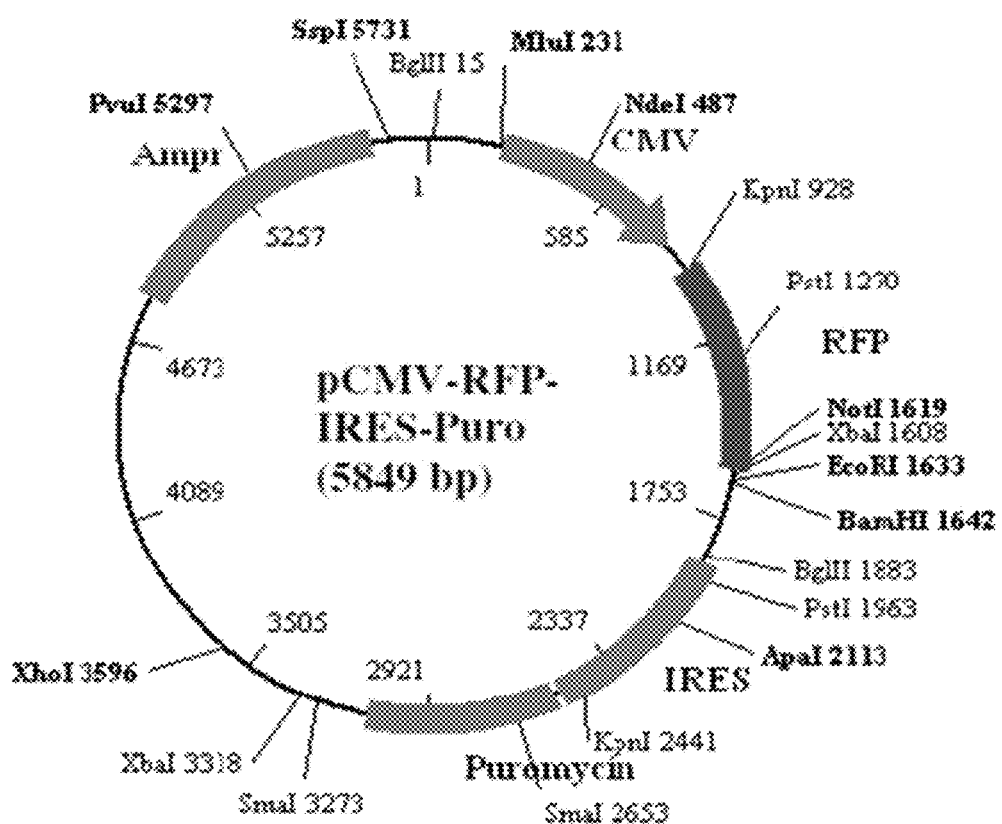

FIG. 19 shows vector map of pCMV-RFP-IRES-Puro.

Figure 20:
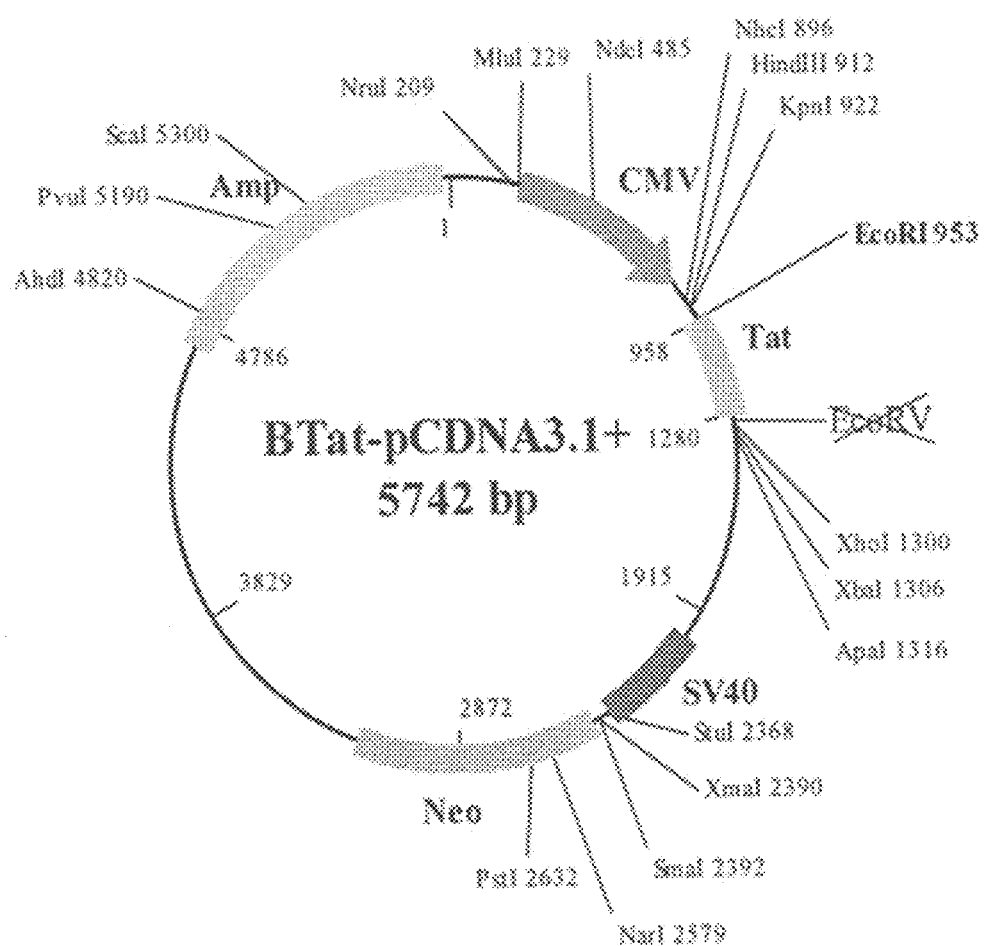

FIG. 20 shows vector map of pCMV-Tat

Figure 21:
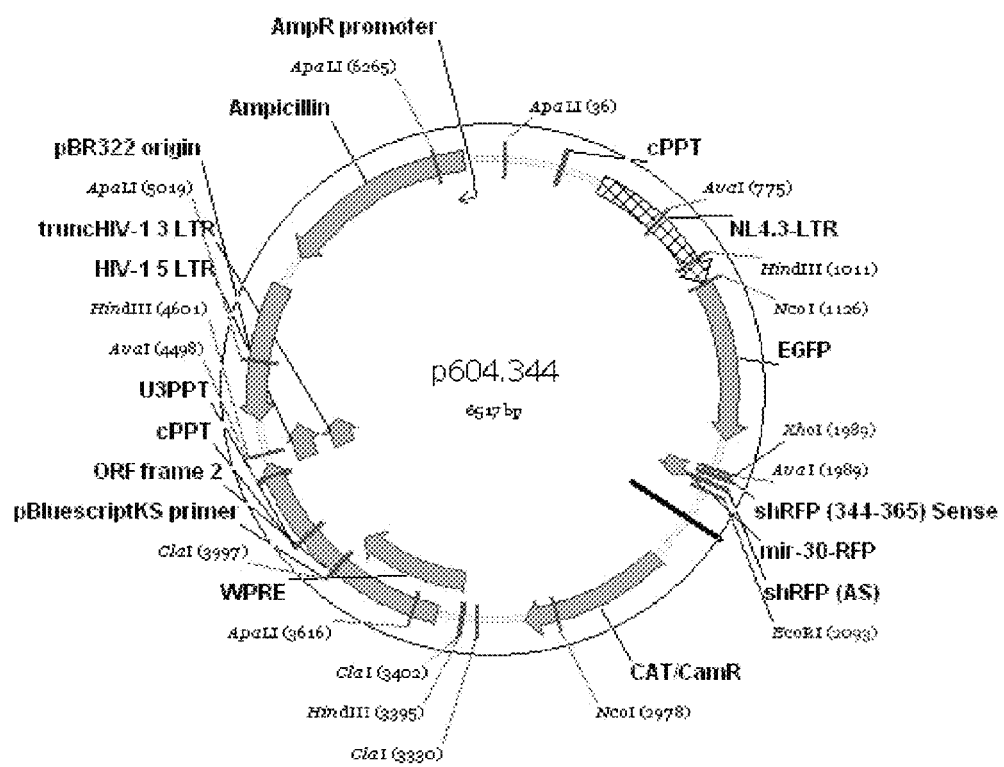

FIG. 21 shows vector map of pCMV-RFP-IRES-Pur

DETAILED DESCRIPTION OF THE DISCLOSURE

The present disclosure relates to a vector comprising nucleotide sequence set forth as Seq ID No. 1 or Seq ID No. 2.

The present disclosure also relates to a method of obtaining vector comprising nucleotide sequence set forth as Seq ID No. 1 or Seq ID No. 2, said method comprising acts of:
 a. obtaining expression vector set forth as Seq ID No. 3; and
 b. inserting heterologous element and Long Terminal Repeat [LTR] sequence into the expression vector to obtain the vector comprising nucleotide sequence set forth as Seq ID No. 1 or Seq ID No. 2.

In an embodiment of the present disclosure, the vector comprising the nucleotide sequence set forth as Seq ID No. 1 or Seq ID No. 2 is Trans activator of transcription [Tat]—inducible Green Flourescent Protein [GFP]—anti Red Flourescent Protein [RFP] short hairpin RNA [shRNA] vector.

In another embodiment of the present disclosure, the heterologous element is shRNA against RFP gene.

In yet another embodiment of the present disclosure, the Seq ID No. 1 comprises shRNA sequence set forth as Seq ID No. 4; and the Seq ID No. 2 comprises shRNA sequence set forth as Seq ID No. 5.

The present disclosure also relates to a vector combination consisting vectors selected from a group comprising nucleotide sequence set forth as Seq ID No. 1 or Seq ID No. 2 or a combination thereof along with:
- a. Reporter Protein expression vector; or
- b. Tat expression vector or
  - any combination thereof.

The present disclosure also relates to a recombinant cell comprising:
- a. vector comprising nucleotide sequence set forth as Seq ID No. 1; or
- b. vector comprising nucleotide sequence set forth as Seq ID No. 2; or
- c. vector of step (a) along with reporter protein expression vector or tat expression vector or any combination thereof; or
- d. vector of step (b) along with reporter protein expression vector or tat expression vector or any combination thereof; or any combination thereof.

The present disclosure also relates to a method of obtaining recombinant cell as claimed in claim 7, said method comprising acts of:
- a. obtaining vector comprising nucleotide sequence set forth as Seq ID No. 1 or Seq ID No. 2;
- b. optionally combining the vector of step (a) or both the vectors of step (a) along with Reporter Protein expression vector or Tat expression vector or any combination thereof; and
- c. transfecting a host cell with the vector vector of step (a) or both the vectors of step (a) or combination of step (b) to obtain the recombinant cell.

The present disclosure also relates to a method of identifying and optionally quantifying viral inhibitor molecule, said method comprising acts of:
a. obtaining vector comprising nucleotide sequence set forth as Seq ID No. 1 or Seq ID No. 2;
b. optionally combining the vector of step (a) or both the vectors of step (a) along with Reporter Protein expression vector or Tat expression vector or any combination thereof;
c. transfecting a host cell with the vector vector of step (a) or both the vectors of step (a) or combination of step (b) to obtain a recombinant cell; and
d. adding inhibitor molecule to the recombinant cell and screening for identifying and optionally quantifying the viral inhibitor molecule.

In another embodiment of the present disclosure, the vector set forth as Seq ID Nos. 1 and 2 are Trans activator of transcription [Tat] -inducible Green Flourescent Protein [GFP]—anti Red Flourescent Protein [RFP] short hairpin RNA [shRNA] vector; and the Reporter Protein expression vector is RFP vector.

In yet another embodiment of the present disclosure, the transfecting is carried out by method selected from group comprising Calcium Chloride method, Electroporation, Microparticle bombardment, Lipofection and Virus mediated transfer; and the host cell is selected from group comprising mammalian cell, eukaryotic cell and prokaryotic cell.

In still another embodiment of the present disclosure, the inhibitor molecule is non-cytotoxic in nature and is selected from group comprising chemicals, natural compounds, pharmaceutical molecules, peptides, aptamers, anti-sense oligos, rhibozymes, siRNA and intracellular antibodies or any combination thereof.

In still another embodiment of the present disclosure, the screening is carried out by up-regulating of RFP along with down regulating of GFP using method selected from group comprising High Throughput Screening, Fluorescence based Screening, and Biochemical based screeing or any combination thereof.

The present disclosure also relates to a kit for identifying and optionally quantifying viral inhibitor molecule or inhibiting Tat, said kit comprising components selected from group having vector as claimed in claim 1, vector combination as claimed in claim 6, cell as claimed in claim 7, Reporter Protein expression vector, Tat expression vector, expression vector set forth as Seq ID No. 3, inhibitor molecule as claimed in claim 13 and instruction manual or any combination thereof.

The present disclosure also relates to a method of assembling a kit for identifying and optionally quantifying viral inhibitor molecule or inhibiting Tat, said method comprising act of combining components selected from group comprising vector as claimed in claim 1, vector combination as claimed in claim 6, cell as claimed in claim 7, Reporter Protein expression vector, Tat expression vector, expression vector set forth as Seq ID No. 3, inhibitor molecule as claimed in claim 13 and instruction manual or any combination thereof.

In an embodiment of the present disclosure, the sample is selected from a group comprising blood, urine, plasma, sweat and stool etc.

In an embodiment of the present disclosure, the method of identifying small molecule inhibitors in standard high throughput screening (HTS) assays using reporter cell lines yielded only a small number of molecules. The disclosure also relates to overcoming basic flaws in the construction of the reporter cell lines used in the HTS which minimized identification of small molecule inhibitors (SMI) with ability to inhibit the function of Tat.

The standard reporter cell lines employ a screening format where expression of the fluorescent protein GFP is down-regulated in the presence of an anti-Tat molecule or Tat inhibitor. A standard HTS based on such a reporter cell line cannot distinguish between a real anti-viral inhibitor and a cytotoxic molecule. Importantly, most of the SMI are likely to be cytotoxic leading to significant attrition rate at a subsequent level.

To circumvent this problem the present disclosure also presents a molecular method which has been developed wherein the expression of a fluorescent protein, RFP (red fluorescent protein), is up-regulated and not down-regulated, in the presence of an anti-Tat molecule or Tat inhibitor. The present method effectively differentiates between anti-viral and cytotoxic compounds since the latter cannot up-regulate the expression of RFP thus efficiently eliminating false hits. In addition to RFP, the cell line retains the original GFP down regulation strategy thus expressing two different fluorescent proteins simultaneously but in an inversely correlated fashion. Higher level expression of RFP in the presence of a Tat-inhibitor is one of the aspects of this invention. Unlike the standard HTS, the present assay is likely to identify non-cytotoxic anti-viral small molecule inhibitors thereby extending the anti-retroviral armamantarium to a viral target.

The present disclosure takes into account that the HTS must inherently differentiate between molecules that have cytotoxic properties and anti-Tat characteristics. Unlike the standard HTS, in the reporter cell lines engineered, the expression of the reporter gene is up-regulated in the presence of a Tat inhibitor. An SMI (Small molecule inhibitor) with cytotoxic properties could down-regulate, but not up-regulate, the reporter gene. Therefore, any SMI that up-regulated the reporter protein possesses a real anti-Tat function. False hits are less in this assay. Furthermore, in the present disclosure the GFP expression is retained in the cell line that follows the standard expression pattern in response Tat. In addition to this, a red fluorescent protein (RFP) is incorporated, whose expression is engineered to manifest in a reciprocal fashion as compared to that of GFP. For instance, when Tat is functional and not inhibited, GFP, but not RFP, is expressed in the cell. In contrast, when Tat is inhibited, GFP is down-regulated with reciprocal and increasing expression of RFP. Progressive expression of RFP as an indicator of Tat inhibition is the main quality of the reporter cells of the present disclosure.

In an embodiment of the present disclosure, Anti-RFP shRNA expression is placed under the control of the LTR and Tat: The reporter cells engineered have two distinct properties which in turn gives an advantage to HTS for Tat. (1) The cells express two different fluorescent proteins simultaneously, GFP and RFP, in a reciprocal manner in response to Tat and (2) up-regulation of RFP expression when Tat is inhibited in a HTS is critical since this is indicative of a Tat inhibitor molecule. To accomplish the pattern of fluorescent protein expression, the following method is used: Two different genetic elements, GFP and anti-RFP shRNA, are engineered under HIV-1 LTR so that they both are simultaneously expressed in the presence of Tat and both are down-regulated when Tat is blocked. Anti-shRNA (a combination of two independent shRNAs both targeting different regions of RFP) specifically and efficiently degrades RFP transcripts in the cell, expressed from an independent gene, thus down-regulating RFP, only in the presence of Tat. This arrangement establishes a reciprocal pattern of gene expression between RFP and anti-RFP shRNA as a function of Tat. When Tat is active anti-RFP shRNA is expressed down-regulating RFP to nearly baseline levels. However, when Tat is inhibited, by a SMI, anti-RFP shRNA is also inhibited, resulting in the restoration of RFP expression in the cell. The stronger the Tat inhibition the higher is the RFP expression.

In an embodiment of the present disclosure, a person skilled in the art can understand that anti-viral molecules refer to viral inihibitor molecules. The same also include small molecule inhibitors.

In an embodiment of the present disclosure a combination of three different plasmid expression vectors is used to achieve the reporter gene expression pattern explained above.

Figure 3:
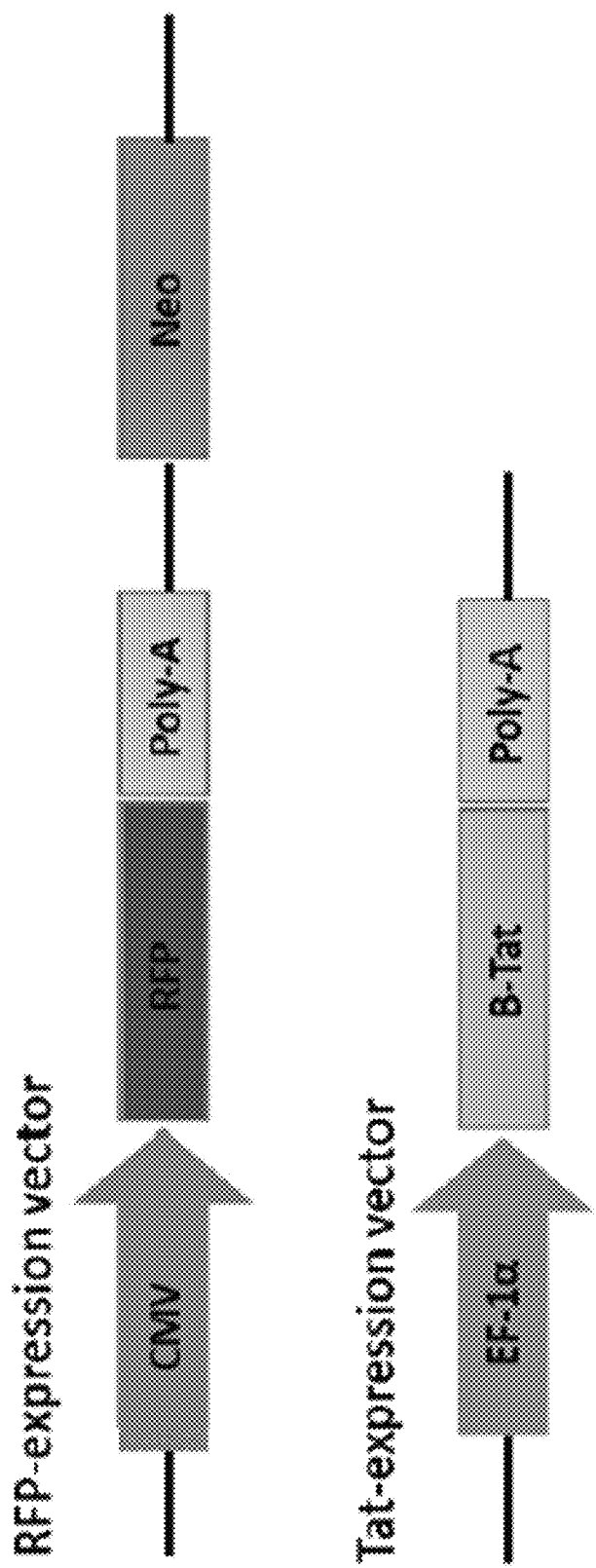
FIG. 3 shows vector schematic for the expression of both RFP and Tat in the cell.

1. RFP-Expression Vector: RFP is expressed under the control of CMV promoter. Expression of the reporter gene is stable and constitutive (FIG. 3). 'Neo' shown here is an independent drug resistance marker which is used for selection of stable cell lines subsequently. Also note that RFP is expressed from an alternative promoter including any of the pol-2 (eg. CMV, RSV, SV-40, beta-actin etc) or -3 (U1, U6, H1, SF etc) classes of eukaryotic promoters that is constitutive or regulatable like tetracycline inducible or suppressible or the like.

2. Tat-Expression Vector: Full-length Tat protein, derived from HIV-1 reference strain NL4-3, is expressed under the CMV promoter. Tat expression is stable and constitutive (FIG. 3). Tat expression vectors under the control of SV40 or EF-1α promoter are also used.

3. GFP and Anti-RFP shRNA Expression Vector: The original shRNA expression vector- pPRIME-LTR-GFP-miRNA—Seq ID No. 3 is used in the instant disclosure. GFP and shRNA are driven by HIV-1 LTR in this vector. Cloning of the anti-RFP siRNA into this vector is done, but faced a consistently high levels of background gene expression given that the original viral promoter is a chimera promoter containing several heterologous elements upstream including CAG enhancer, CMV enhancer and others (see top panel of FIG. 4). Additional heterologous elements are engineered as a safety measure to prevent regeneration of replication competent viruses from the experiments. These additional elements not only made the viral promoter Tat-non-responsive but also promiscous in developing high background gene expression even if Tat is not present (FIG. 5). To make gene expression Tat-responsive, an additional authentic LTR from a reference HIV-1 subtype B molecular clone (NL4-3) is inserted upstream of GFP (FIG. 4, B-LTR). The new vector is called pPRIME-LTR 2-GFP-mi RNA also termed as vector comprising nucleotide sequence set forth as Seq ID Nos. 1 and 2. Following this modification, the new vector expressed high level GFP in a Tat-inducible manner, suggesting background gene expression is not an issue any longer (FIG. 5).

Anti-RFP shRNAs: Several shRNA molecules targeting RFP gene sequence are designed as summarized in Table-1.

TABLE 1

Sequences of RFP targeted by the shRNA molecules designed in the present disclosure

| Plasmid | Target nucleotide sequence on REP (5' to 3') | SEQ ID NO: | Nucleotide coordinates |
|---|---|---|---|
| p603 | CCCTGCCCTTCCCCTGGGACAT | 6 | 157-179 |
| p603.14 | AGAACGTCATCACCGAGTTCAT | 7 | 14-35 |
| p603.344 | ACGGCTGCTTCATCTACAAGGT | 4 | 344-365 |
| p603.515 | ACTACCTGGTGGAGTTCAAGTC | 8 | 515-536 |
| p603.620 | ACTACACCATCGTGGAGCAGTA | 5 | 620-641 |

Each of these shRNA sequences is cloned between restriction enzyme sites XhoI and EcoRI thus grafting this sequence into the upper hairpin of the original miR30 miRNA (FIG. 6). When expressed in the cell, the miRNA is processed by the host machinery releasing the shRNA that binds and degrades the target mRNA specifically thus down regulating the protein expression of the target gene specifically and in a dose-dependent manner The two different pPRIME-LTR-GFP: anti-RFP miRNA vectors are identical except for the specific anti-RFP miRNA sequences that target two different sequences in the RFP transcript. One of the miRNAs targets the sequence of RFP spanning nucleotides 344-365 and the other 620-641. The RFP gene is derived from a commercial vector pdsRED2-Nuc. The co-ordinates of important features of the plasmid is given below:

Vector Co-Ordinates:

| LTR - 480 bp | 1,113 bp |
|---|---|
| GFP - 1,127 bp | 1,846 bp |
| miRNA RFP | 1,994 bp-2,091 bp |
| shRNA RFP | Sense 2,013-2,034 bp |
| | Antisense 2,054-2,075 bp |

Using a combination of these three above vectors, several experiments are performed to prove the concept.

TABLE 2

The basic experimental format of reporter cell assay depicting how RFP expression is expressed, suppressed and recovered in the cells. Expression of GFP is reciprocally related to that of RFP.

| No | Vector combination | RFP expression | GFP expression | Explanation |
|---|---|---|---|---|
| 1 | RFP-expression vector + Anti-RFP shRNA expression vector | Expressed | Not expressed | RFP expressed since there is no Tat to switch on the anti-RFP shRNa |
| 2 | RFP-expression vector + Anti-RFP shRNA expression vector + Tat-expression vector | Suppressed | Expressed | RFP suppressed as Tat switched on shRNA |
| 3 | RFP-expression vector + Anti-RFP shRNA expression vector + Tat-expression vector + Tat inhibitor | Recovered | Suppressed | Tat inhibitor blocks Tat which in turn relieves RFP suppression |

The instant experiments are categorized into two distinct phases. (1) Transient transfection assays in host cells such as HEK293 cells using calcium chloride format.

Several SMI with or without known inhibitory properties for Tat are used. (2) Establishing HeLa stable cells using the combination of three groups of the plasmids described above.

The experiments are divided into two sequential phases. In the first phase, examining the potential of the shRNA to down-regulate RFP specifically in the cells in the presence of Tat but in the absence of a Tat inhibitor is done (see Table-2). A specific combination of two independent shRNAs is identified to be the best to achieve this objective (FIGS. 7 and 8). The present disclosure revealed that shRNA combination 603.344 and 603.620 suppressed RFP expression to the least extent thus showing a synergistic effect. Hence, the combination of these two shRNAs are used for the subsequent experiments.

In the second phase, using small molecule inhibitors, with or without anti-Tat activities, the inhibition of RFP gene expression is relieved (FIG. 12). Several small molecule inhibitors reported in the literature are used in these experiments.

In an embodiment of the present disclosure, Cytotoxic molecules down-regulate GFP but do not up-regulate RFP. In the HTS assays thus far, down-regulation of GFP is considered as an indication for the presence of a Tat inhibitor. For instance prior research presented testing of three known Tat inhibitors for the down-regulation of GFP. This study also did a separate tetrazolium-based assay for cell viability which is indicative of cytotoxicity of the compound. Of note, an assay for cytotoxicity cannot be incorporated into a HTS considering the costs and efforts especially when screening thousands of molecules. In the above mentioned study the researchers found that with increasing concentrations of the inhibitors, GFP expression is down-regulated (FIG. 9). This inference may or may not be applicable when a large number of molecules of unknown properties are being screened. Importantly, down-regulation of GFP need not necessarily be indicative of a Tat inhibitor as the present disclosure gives the data below in the examples. In an embodiment of the present disclosure a Tat inhibitor enhances RFP expression significantly (above 3 SD [Splice Donor] of a well with only parental cells). In addition, the Tat inhibitor may or may not down modulate GFP. A simple mathematical formula as shown below captures the up-regulation of RFP in the presence or absence of GFP gene modulation when exposed to a SMI.

Differential expression in the presence of Tat=(RFP/GFP) with Tat

Differential expression in the absence of Tat (RFP/GFP) without Tat

In an embodiment of the present disclosure, when the above figure is above 5, it indicates the presence of a Tat inhibitor molecule.

In an embodiment of the present disclosure, the identification of the inhibitors is followed by quantification of the same methods selected from a group comprising fluorescence microscopy, fluorimetry and flowcytometry.

A more complete understanding can be obtained by reference to the following specific examples, which are provided for purposes of illustration only and are not intended to limit the scope of the disclosure.

EXAMPLES

Example 1

Designing the Expression Vectors and Vector Combinations A) CMV-RFP expression vector: The RFP gene from a commercial vector is amplified using dsRED as template and PCR primers N668 and N669. The PCR fragment is cloned into the EcoRV site of another commercial vector pIRES-Puro. The RFP gene expression in this vector is thus controlled by the CMV promoter (FIG. 19

Primer Information

```
N668 (FP; SEQ ID NO: 9):
  Overhang KpnI
5'CTAGTAGGTACCATGGCCTCCTCCGAGAACGTC 3' (S)

N669 (RP; SEQ ID NO: 10):
  Overhang XbaI
5'AGCCGTTCTAGACTACAGGAACAGGTGGTGGCG 3' (RC)
```

B) CMV-Tat Vector: The full-length Tat cDNA from molecular clone YU-2 (subtype-B) is made from cellular RNA of 293 cells transfected with the viral plasmid clone. PCR is performed using a primer pair N531 and N113 and the PCR product is directionally cloned into pcDNA3.1 vector between EcoRI and EcoRV sites. In the final vector, Tat expression is under the control of the CMV promoter (FIG. 20).

Primer Information

N113 (FP; SEQ ID NO: 11):
      Kozak sequence
5' TAGAATTCGCCGCCGCCATGGAGCCAGTAGATCCTAACCT
A 3' (S)

N531 (RP; SEQ ID NO: 12):
 Overhang BamHI
5' AGAAGCGGATCCCTAATGGACCGGATCTGTCTCTGT 3' (RC)

C) pPRIME-LTR-GFP: anti-RFP miRNA vectors (Tat-inducible GFP-anti RFP shRNA vector): The final vectors are made from the parental vectors through several steps. The original pPrime-LTR-GFP-miRNA vector is designed for lenti vector production. This vector has multiple problems and is not suitable for Tat-mediated gene expression regulation. The main problem is its promoter, the 5'-LTR is a chimera consisting of multiple regulatory elements including a CMV enhancer upstream. Hence it gives a lot of background gene expression. Hence, a lot of engineering is done to counter the problem of background and lack of Tat-responsiveness.

TABLE 3

Anti-RFP shRNA sequences and their coordinates in the RFP gene

| Plasmid | Target nucleotide sequence in RFP | SEQ ID NO: | Nucleotide coordinates |
|---|---|---|---|
| p603.14 | AGAACGTCATCACCGAGTTCAT | 7 | 14-35 |
| p603.515 | ACTACCTGGTGGAGTTCAAGTC | 8 | 515-536 |
| p603.344 | ACGGCTGCTTCATCTACAAGGT | 4 | 344-365 |
| p603.620 | ACTACACCATCGTGGAGCAGTA | 5 | 620-641 |

Tat-Inducible GFP-Anti RFP shRNA Vector:
(1) shRNA cloning: 4 different anti-RFP shRNAs are cloned (Table-3) into the original parental vector between XhoI and EcoRI sites.
(2) A viral promoter (LTR) from the standard subtype-B viral clone NL4-3 is amplified in PCR and placed upstream of the GFP cassette. In these vectors, expression of GFP and anti-RFP shRNA are thus placed under the control of NL4-3 LTR which is Tat-responsive and offers less background fluorescence problem as compared to the original vectors.
(3) The entire cassette of the original chimera LTR and up to the RRE element is deleted. The final vector map of pPRIME-LTR-GFP: anti-RFP miRNA (p604.344) is presented in FIG. 20. The map for pPRIME-LTR-GFP: anti-RFP miRNA (p604.620) is similar. See pPRIME-LTR-GFP-anti-RFPmiRNA plasmid sequences of these two vectors mentioned in sequence listing section as Seq ID Nos. 1 and 2 in the instant disclosure.

Example 2

Transfecting the Cell with the Vector Combination Followed by Addition of Tat Inhibitors Vector DNA Transfection: All the proof-of-the-concept assays embedded in this document are performed using the transient transfection method formats. Most of the experiments are done using host cells such as HEK293 cells and preferably the standard calcium transfection protocol. Further, few experiments are also performed using HeLa cells. A commercial lipid formulation is used for this and is used following the suppliers instructions.

siRNA Transfection: Anti-Tat siRNA molecules are introduced into cells using a commercial lipid-nanoparticle formulation as per the instructions from the supplier.

Adding Tat Inhibitors to the Cell and Screening to Identify Anti-viral/Tat Molecules: The assays are performed using the following format although several variations are introduced depending on the need.
a) Cell Plating: Cells are plated in 96-well culture plates the previous evening and on the morning of the experiment, they are at 30-40% occupancy and in the logarithmic growth phase.
b) DNA Vector Transfection: A combination of 4 vectors is used in most of the assays. The total DNA concentration ranged from 1 to 2 μg per a 24-well plate or 100-200 ng per 96-well plate depending on the context.
1. Anti-RFP siRNA vector (pPRIME-LTR-GFP: anti-RFP miRNA (p604.344):100-600 ng
2. Anti-RFP siRNA vector (pPRIME-LTR-GFP: anti-RFP miRNA (p604.620): 100-600 ng
3. CMV-Tat (YU-2) vector:50-200 ng
4. CMV-RFP vector (pCMV-RFP-IRES-Puro) (FIGS. 21): 50-200 ng Cells are monitored for GFP or RFP expression after 24 h after subjected to an anti-Tat compound.

Anti-Tat Compound Treatment: A small molecule inhibitor (at concentrations mentioned in individual experiments above) or anti-Tat siRNA (20-100 ng per well) are used. The anti-Tat agent is used immediately after plasmid DNA transfection or after 12-24 h. Cells are removed from the wells by trypsinization and made into single cell suspension in phosphate buffered saline. The mean fluorescence intensity of the cells was determined using flow cytometry. Alternatively, cells were removed from the well using trypsinization and suspended in PBS. The intensity of the fluorescence was quantitatively determined using a standard fluorimeter. Fluorescent protein gene expression is measured at 24, 36, 48 and 72 h from vector transfection, at one time point or multiple time points.

Example 3

Showing GFP Down Regulation in Presence of Cytotoxic Molecules but No up-regulation of RFP Gene in the Presence of the Same DRB (5, 6-dichloro-1-beta-D-ribofuranosylbenzimidazole) a small molecule inhibitor, blocks an essential cellular enzyme CDK9, a kinase, critical for general transcription of many genes and therefore is cytotoxic. CDK 9 is also necessary for Tat function hence may or may not function as a potential Tat inhibitor. The Tat inhibition potential as well as cytotoxicity of DRB at 3 different concentrations is tested in HEK 293 cells using plasmid combinations as defined in Table-2. Images of the cells are captured using light microscopy, GFP or RFP filters at 36 h. A progressive down-regulation of GFP expression is noted with increasing concentration of DRB (Figure-10, middle panel). Importantly, significant levels of cell death also noticed with increasing concentration of DRB especially at 80 μM concentration (light microscopy images, left panels). Of note, there is no concomitant up-regulation of RFP expression with increasing concentration of DRB. Taken together, these data suggest that GFP down-regulation is an event related to the cytotoxic properties of DRB rather than to anti-Tat function. Thus, the GFP-based assay identifies false hits, but not the instant RFP-based assay.

Example 4

Use of Small Molecule Inhibitor WP631

A different small molecule inhibitor WP631 which is antagonistic to cellular transcription factor Sp1 is not only toxic to the cell at higher concentrations but also marginally reduced GFP expression (FIG. 11). Although a small relief in RFP suppression is evident, this is not significant. The noted minor recovery of RFP expression may be attributed to the functional association of Tat with that of Sp1. The correlation between apoptosis and GFP down-regulation is noteworthy.

The two experiments shown above and several other not shown here established that GFP down-regulation need not necessarily allude to the presence of an anti-Tat inhibitor molecule. Given that small molecule inhibitors with absolute specificity are few and commercially not available, siRNA targeting the Tat nucleotide sequence is designed. When Tat is destroyed by specific siRNA, the RFP expression should be restored since anti-RFP shRNA are not synthesized any longer. As shown in FIG. 12, RFP expression is reduced in the presence of Tat (since anti-RFP shRNA is expressed) and GFP expression increased. However, in the presence of anti-Tat siRNA (20 nM), the RFP expression is relieved significantly without significant cell toxicity. A scrambled siRNA did not recover RFP expression suggesting assay specificity. Of note, in this specific experiment, there is no significant reduction of GFP in the presence of anti-Tat siRNA.

The experiments presented above collectively provide experimental evidence that the new reporter assay developed in the present disclosure is substantially and radically different from the existing art and can differentiate between genuine anti-Tat inhibitor molecules and the undesirable cytotoxic compounds. This assay thus offers a great advantage for high throughput screening to find anti-Tat inhibitor molecules.

Example 5

Shows the Up-regulation of RFP in Presence of Real Tat Inhibitor

Since there are not many small-molecule inhibitors specific to Tat, and none of them are available commercially, as a way out, a siRNA specifically targeting Tat is designed. siRNA are small double-stranded RNA molecules that bind to target sequence specifically and degrade it in the cell or block its activity. Two complementary and synthetic RNA oligo-nucleotides are annealed and used with a commercial lipid, in the assay. The advantage of siRNA is their specificity for the target gene. Use of siRNA helps us overcome the non-availability of Tat-specific SMI but still serves as proof-of-the-concept. As is seen from this experiment, in the absence of Tat, RFP is expressed (Top panel). When Tat-expression vector is included in the assay, RFP is down regulated, since Tat induces expression of anti-RFP miRNA, and GFP is expressed (middle panel). Importantly, in the presence of 20 nM anti-Tat siRNA N1420-1, RFP recovery is evident (bottom panel) although not to the original levels given the nature of the transfection.

GFP down regulation is not evident as this is transient transfection and abundant quantities of GFP are already made by the cell. Scrambled control siRNA does not relieve RFP expression suggesting specificity of the result. Furthermore, light microscopy images do not show cytotoxicity due to anti-Tat siRNA suggesting safety (not shown). The experiment thus proves that a small molecule inhibitor specific for Tat efficiently relieves RFP expression from the reporter cell.

TABLE 4

Anti-Tat siRNA design. Three different siRNA molecules (consisting of two pairs of oligo-nucleotides for each), have been presented. The oligonucleotide sequences, the sequence coordinates and the taget domains in Tat have been shown.

| siRNA name | Sequence (5' to 3') | SEQ ID NO: | Coordinates on YU-2 (Accn No. M93258) | Target on Tat |
|---|---|---|---|---|
| N1398-9 | 5' CUGCUUGUACCAAUUGCUAdTdT | 13 | 5889-5907-dTdT | N-terminal region through Cysteine-rich domain |
|  | 5' UAUGGCAGGAAGAAGCGGAdTdT | 14 | dTdT-5889-5907 |  |
| N1400-1 | 5' UAUGGCAGGAAGAAGCGGAdTdT | 15 | 5969-5987-dTdT | Basic region |
|  | 5' UCCGCUUCUUCCUGCCAUAdTdT | 16 | dTdT-5969-5987 |  |
| N1402-3 | 5' GAAGCGGAGACAGCGACGAdTdT | 17 | 5980-5995-dTdT | Basic region |
|  | 5' UCGUCGCUGUCUCCGCUUCdTdT | 18 | dTdT-5889-8557 |  |

Example 6

Shows Up-regulation of RFP and Simultaneous Down-regulation of GFP in Presence of Real Tat Inhibitor Three different anti-Tat siRNAs as summarized in Table-4 are designed. Results of the transient transfection confirm specific anti-Tat activity of all the siRNA molecules but not the scrambled RNA (FIG. 13).

The assay also identifies SMI which inhibit cellular factors needed for Tat. 5,6-Dichlorobenzimidazole Riboside (DRB) is a potent inhibitor of CDK9 which is a cellular factor necessary for Tat function. DRB at 25 µM concentration relieves Tat-mediated RFP suppression (FIG. 14). A relative down regulation of GFP is also evident. Thus the assay of the present disclosure also identify such SMI that have an indirect effect on Tat function.

A different SMI WP631 an inhibitor of cellular factor Sp1 also fall under this category as Sp1 and Tat coordinate to regulate gene expression from the viral promoter. As seen in FIG. 15, WP631 treatment partially relieves Tat-mediated inhibition of RFP at 100 nM concentration. Low level cytotoxicity is also evident as the thinning of the cell density under light microscopy.

Example 7

Shows No Effect on RFP Regulation When Only Cytotoxic Molecule is Used

Flavipiridol is a small molecule inhibitor (SMI) of cellular CDK kinases needed for various physiological functions. CDK kinases are a class of enzymes essential for the routine biological functions of cells. For instance, this group of enzymes adds a phosphate group to proteins or DNA under different conditions. Such chemical modifications impart differential biochemical properties to the target molecules so that they acquire different biological properties. Blocking functions of such important cellular enzymes using specific SMI can be toxic to the cells. Some of these kinases are needed for the functioning of Tat. Logically, by blocking those specific enzymes, Tat function can indirectly can be blocked. But, these enzymes are also needed for other essential cellular functions. Hence such SMI can in general be cytotoxic. Treating cells with increasing concentrations of falvipiridol leads to progressive increase in cytotoxicity but not to RFP gene expression.

Example 8

Shows GFP is Down-regulated Not Only by Presence of Tat Inhibitor but also in Presence of Cytotoxic Molecules Roscovitine is another SMI of similar inhibitory properties which inhibits a range of cellular CDK kinases necessary for regular cellular functions. Application of roscovitine at a concentration of 3 µM leads to cytotoxicity which is manifested in the reduced expression of GFP but not in enhanced expression of RFP (FIG. 17).

Likewise, LTK14, a derivative of garcinol, is an SMI that inhibits essential cellular factors histidine acetyl transferases. Increasing concentration of LTK14 cause progressively increased cell death and down regulation of GFP, but not enhanced RFP expression (FIG. 18).

Example 9

Shows Simultaneous Evaluation of Real Tat Inhibitors and Cytotoxic Molecules Protocol Tat-responsive reporter cells are plated in 96-well black microplates (Corning Costar) at a density of 10,000-20,000 cells/200 µl of RPMI medium devoid on phenol red but supplemented with penicillin/streptomycine, glutamine and 10% fetal calf serum per well using a multi-channel pipette.

Cells are incubated for 24 h in a $CO_2$ incubator at 5% $CO_2$ concentration, 37° C. and 100% humidity. At this time the cells must be well attached to the plastic surface and express GFP but not RFP.

A library of small molecule inhibitors is applied to the plates either using a multi-channel pipettes or robotic automated devices at concentration that ranges from nM to µM of the SMI. Plates are returned to the incubator and maintained under culture conditions for 12-24 h. Appropriate controls are used including wells with standard SMI known to inhibit Tat function at suitable concentrations.

GFP and RFP expression is monitored under a fluorescent microscope fitted with a UV laser, suitable emission filters and a digital camera. Background fluorescence is subtracted for GFP or RFP using parental cells that do not express either of these fluorescent proteins.

Any wells where RFP expression is up-regulated above mean plus 3 SD of control wells without SMI is selected for further evaluation.

---

I claim:

1. A purified vector comprising the nucleotide sequence set forth as Seq ID No. 1 or Seq ID No. 2.

2. A method of obtaining a purified vector comprising nucleotide sequence set forth as Seq ID No. 1 or Seq ID No. 2, said method comprising acts of:
   a. obtaining expression vector set forth as Seq ID No. 3; and
   b. inserting a heterologous element and Long Terminal Repeat [LTR] sequence into the expression vector to obtain the purified vector comprising nucleotide sequence set forth as Seq ID No. 1 or Seq ID No. 2.

3. The purified vector as claimed in claim 1, wherein the purified vector comprising the nucleotide sequence set forth as Seq ID No. 1 or Seq ID No. 2 is a Trans activator of transcription [Tat] -inducible Green Fluorescent Protein [GFP] -anti Red Fluorescent Protein [RFP] short hairpin RNA [shRNA] vector.

4. The purified vector as claimed claim 1, further comprising a heterologous element, wherein the heterologous element is a shRNA against an RFP gene.

5. The purified vector as claimed in claim 1, wherein the Seq ID No. 1 comprises a shRNA sequence set forth as Seq ID No. 4; and the Seq ID No. 2 comprises a shRNA sequence set forth as Seq ID No. 5.

6. A purified vector combination consisting of purified vectors selected from the group consisting of nucleotide sequences set forth as Seq ID No. 1, Seq ID No. 2 and combinations thereof along with:
   a. Reporter Protein expression vector; or
   b. Tat expression vector or any combination thereof.

7. A recombinant cell comprising:
   a. a vector comprising a nucleotide sequence set forth as Seq ID No. 1; or
   b. a vector comprising a nucleotide sequence set forth as Seq ID No. 2; or
   c. the vector of (a) along with a reporter protein expression vector or Tat expression vector or any combination thereof; or
   d. the vector of (b) along with a reporter protein expression vector or Tat expression vector or any combination thereof; or any combination thereof.

8. A method of obtaining the recombinant cell as claimed in claim 7, said method comprising acts of:
   a. obtaining a vector comprising the nucleotide sequence set forth as Seq ID No. 1 or Seq ID No. 2;
   b. optionally combining the vector of step (a) or both the vectors of step (a) along with Reporter Protein expression vector or Tat expression vector or any combination thereof; and
   c. transfecting a host cell with the vector of step (a) or both the vectors of step (a) or combination of step (b) to obtain the recombinant cell.

9. A method of identifying and optionally quantifying a viral inhibitor molecule, said method comprising acts of:
   a. obtaining a vector comprising the nucleotide sequence set forth as Seq ID No. 1 or Seq ID No. 2;
   b. optionally combining the vector of step (a) or both the vectors of step (a) along with Reporter Protein expression vector or Tat expression vector or any combination thereof;
   c. transfecting a host cell with the vector of step (a) or both the vectors of step (a) or combination of step (b) to obtain a recombinant cell; and
   d. adding an inhibitor molecule to the recombinant cell and screening for, identifying, and optionally quantifying the viral inhibitor molecule.

10. The purified vector combination as claimed in claim 6 or the cell as claimed in claim 7 and methods as claimed in claims 8 and 9; wherein the vectors set forth as Seq ID Nos. 1 and 2 are Trans activator of transcription [Tat] -inducible Green Flourescent Protein [GFP] -anti Red Flourescent Protein [RFP] short hairpin RNA [shRNA] vector; and a Reporter Protein expression vector is RFP vector.

11. The methods as claimed in claim 8 or 9, wherein the transfecting is carried out by a method selected from the group consisting of Calcium Chloride method, Electroporation, Microparticle bombardment, Lipofection and Virus mediated transfer; and the host cell is selected from the group consisting of mammalian cell, eukaryotic cell and prokaryotic cell.

12. The method as claimed in claim 9, wherein the inhibitor molecule is non-cytotoxic in nature and is selected from the group consisting of chemicals, natural compounds, pharmaceutical molecules, peptides, aptamers, anti-sense oligos, rhibozymes, siRNA, intracellular antibodies, and combinations thereof.

13. The method as claimed in claim 9, wherein the screening is carried out by up-regulating RFP along with down regulating GFP using a method selected from the group comprising consisting of High Throughput Screening, Fluorescence based Screening, Biochemical based screening, and combinations thereof.

14. A kit for identifying and optionally quantifying a viral inhibitor molecule or inhibiting Tat, said kit comprising the vector as claimed in claim 1 and components selected from the group consisting of a recombinant cell comprising a vector comprising the nucleotide sequence set forth as SEQ ID No. 1 or Seq ID No. 2, a Reporter Protein expression vector, a Tat expression vector, an expression vector set forth as Seq ID No. 3, a Trans activator of transcription [Tat] -inducible Green Fluorescent Protein [GFP] -anti Red Fluorescent Protein [RFP] short hairpin RNA [shRNA] vector comprising the nucleotide sequence of Seq ID No. 1 or Seq ID No. 2, an inhibitor molecule, an instruction manual, and combinations thereof.

15. A method of assembling a kit for identifying and optionally quantifying a viral inhibitor molecule or inhibiting Tat, said method comprising combining the vector as claimed in claim 1 and components selected from the group consisting of a recombinant cell comprising a vector comprising the nucleotide sequence set forth as SEQ ID No. 1 or Seq ID No. 2, a Reporter Protein expression vector, a Tat expression vector, an expression vector set forth as Seq ID No. 3, a Trans activator of transcription [Tal] -inducible Green Fluorescent Protein [GFP] -anti Red Fluorescent Protein [RFP] short hairpin RNA [shRNA] vector comprising the nucleotide sequence of Seq ID No. 1 or Seq ID No. 2, an inhibitor molecule, an instruction manual, and combinations thereof.

16. The method as claimed in claim 2, wherein the purified vector comprising the nucleotide sequence set forth as Seq ID No. 1 or Seq ID No. 2is a Trans activator of transcription [Tat]-inducible Green Fluorescent Protein [GFP]-anti Red Fluorescent Protein [RFP] short hairpin RNA [shRNA] vector.

17. The method as claimed in claim 2, wherein the heterologous element is a shRNA against an RFP gene.

18. The method as claimed in claim 2, wherein the Seq ID No. 1 comprises a shRNA sequence set forth as Seq ID No. 4; and the Seq ID No. 2 comprises a shRNA sequence set forth as Seq ID No. 5.

19. The methods as claimed in claim 8 or 9; wherein the vectors set forth as Seq ID Nos. 1 and 2 are Trans activator of transcription [Tat]-inducible Green Fluorescent Protein [GFP]-anti Red Fluorescent Protein [RFP] short hairpin RNA [shRNA] vector; and a Reporter Protein expression vector is RFP vector.

* * * * *